US011346829B2

(12) United States Patent
Suslick et al.

(10) Patent No.: US 11,346,829 B2
(45) Date of Patent: May 31, 2022

(54) METHODS AND DEVICES FOR DETECTION OF TRIMETHYLAMINE (TMA) AND TRIMETHYLAMINE OXIDE (TMAO)

(71) Applicant: The Board of Trustees of the University of Illinois, Urbana, IL (US)

(72) Inventors: Kenneth S. Suslick, Champaign, IL (US); Zheng Li, Urbana, IL (US); Maria K. LaGasse, Lenexa, KS (US)

(73) Assignee: The Board of Trustees of the University of Illinois, Urbana, IL (US)

(*) Notice: Subject to any disclaimer, the term of this patent is extended or adjusted under 35 U.S.C. 154(b) by 280 days.

(21) Appl. No.: 15/598,257

(22) Filed: May 17, 2017

(65) Prior Publication Data

US 2017/0336379 A1 Nov. 23, 2017

Related U.S. Application Data

(60) Provisional application No. 62/338,063, filed on May 18, 2016.

(51) Int. Cl.
| | |
|---|---|
| *G01N 33/12* | (2006.01) |
| *G01N 21/78* | (2006.01) |
| *G01N 33/487* | (2006.01) |
| *G01N 31/22* | (2006.01) |
| *G01N 21/80* | (2006.01) |

(52) U.S. Cl.
CPC .......... *G01N 33/12* (2013.01); *G01N 21/78* (2013.01); *G01N 33/487* (2013.01); *G01N 21/80* (2013.01); *G01N 31/22* (2013.01); *G01N 31/221* (2013.01); *G01N 2201/0221* (2013.01)

(58) Field of Classification Search
CPC ...... G01N 33/487; G01N 21/78; G01N 33/12; G01N 31/22; G01N 21/80; G01N 31/221
USPC .................................................. 436/111–112
See application file for complete search history.

(56) References Cited

U.S. PATENT DOCUMENTS

| 3,954,809 A * | 5/1976 | Deyoe ................ C07D 307/62 |
| | | 549/317 |
| 4,201,548 A * | 5/1980 | Tamaoku .............. G01N 31/22 |
| | | 422/421 |
| 4,839,352 A * | 6/1989 | Barash ................ C07D 205/08 |
| | | 210/210 |

(Continued)

FOREIGN PATENT DOCUMENTS

WO 2015034801 A2 3/2015

OTHER PUBLICATIONS de la Huerga, J. et al, Journal of Clinical Inverstigation, 1951 30, 463-470.*

(Continued)

*Primary Examiner* — Arlen Soderquist
(74) *Attorney, Agent, or Firm* — Klintworth & Rozenblat IP LLP

(57) ABSTRACT

The present disclosure provides methods for detection and quantification of trimethylamine (TMA) or trimethylamine oxide (TMAO) comprising passing a sample over a sensor comprising a substrate having a plurality of chemically responsive dyes selected from the following classes of chemically responsive dyes: metal-containing dyes, pH indicators, or solvatochromic/vapochromic dyes. The disclosure also provides devices and sensors for the detection and quantification of TMA, and methods of diagnosing a subject having trimethylaminuria (TMAU).

17 Claims, 36 Drawing Sheets

(56) References Cited

U.S. PATENT DOCUMENTS

| | | | |
|---|---|---|---|
| 6,368,558 B1* | 4/2002 | Suslick | G01N 21/272 422/404 |
| 6,495,102 B1* | 12/2002 | Suslick | G01N 21/272 422/404 |
| 7,261,857 B2* | 8/2007 | Suslick | G01N 21/272 422/400 |
| 8,852,504 B2* | 10/2014 | Suslick | C12Q 1/04 422/50 |
| 9,204,821 B2* | 12/2015 | Martino | A61B 5/097 |
| 9,862,985 B2* | 1/2018 | Lim | C12Q 1/04 |
| 9,880,137 B2* | 1/2018 | Lim | G01N 21/253 |
| 2003/0129085 A1* | 7/2003 | Suslick | G01N 21/272 422/400 |
| 2003/0143112 A1* | 7/2003 | Suslick | G01N 21/272 422/400 |
| 2003/0166298 A1* | 9/2003 | Suslick | G01N 21/272 436/169 |
| 2004/0184948 A1* | 9/2004 | Rakow | G01N 21/45 422/1 |
| 2006/0257285 A1* | 11/2006 | Burdon | G01N 21/78 422/400 |
| 2008/0050839 A1* | 2/2008 | Suslick | A61B 5/083 436/164 |
| 2008/0199904 A1* | 8/2008 | Suslick | C12Q 1/04 435/34 |
| 2009/0035179 A1* | 2/2009 | Rakow | G01N 21/78 422/400 |
| 2010/0166604 A1* | 7/2010 | Lim | G01N 21/253 422/400 |
| 2013/0281515 A1* | 10/2013 | Coady | A61K 31/17 514/44 R |
| 2013/0303929 A1* | 11/2013 | Martino | A61B 5/097 600/532 |
| 2017/0102335 A1 | 4/2017 | Suslick et al. | |

OTHER PUBLICATIONS

Bystedt, J. et al, Journal of the Science of Food and Agriculture 1959, 10 301-304.*
Herschdoefer, S, M, et al, Analyst 1979, 104, 434-450.*
Norin, H. et al, Chemosphere 1985, 14, 313-323.*
Raymond, J. A., Fish Physiology and Biochemistry 1994, 13, 13-22.*
Marner, O. A. et al, Analytical Biochemistry 1999, 276, 144-149.*
Øverland, M. et al, Journal of Animal Science 1999, 77, 2143-2153.*
Rakow, N.A. et al, Nature 2000, 406, 710-714.*
Byrne, L. et al., Analyst 2002, 127, 1338-1341.*
Lau, K. T.. et al, Sensors and Actuators B 2004, 98, 12-17.*
Rakow N. A. et al., Angewandte Chemie International Edition 2005, 44, 4528-4532.*
Gulino, A. et al, Chemistry of Materials 2005, 17, 4043-4045.*
Pacquit, A. et al, Talanta 2006, 69, 515-520.*
Janzen, M. C. et al, Analytical Chemistry 2006, 78, 3591-3600.*
Alimelli, A. et al., Analytica Chimica Acta 2007, 582, 320-328.*
Mazzone, P. J. et al, Thorax 2007, 62, 565-568.*
Lim, S. H. et al, Organic Letters 2008, 10, 4405-4408.*
Bang, J. H. etal, Langmuir 2008, 24, 13168-13172.*
Musto, C. J. et al, Analytical Chemistry 2009, 81, 6526-6533.*
Lim, S. H. et al, Nature Chemistry 2009, 1, 562-567 and 19 pages of supplementary material.*
Suslick, B. A. et al, Analytical Chemistry 2010, 82, 2067-2073.*
Feng, L. et al, Chemical Communications 2010, 46, 2037-2039 and 18 pages of supplementary material.*
Tang, Z. et al, Sensors 2010, 10, 6463-6476.*
Gowda, N. B. et al, Tetrahedron Letters 2010, 51, 5690-5693.*
Feng, L. et al, Analytical Chemistry 2010, 82, 9433-9440.*
Huang, X. et al, Journal of Food Engineering 2011, 105, 632-637.*
Carey, J. R. et al, Journal of the American Chemical Society 2011, 133, 7571-7576.*
Lin, H, et al, Journal of the American Chemical Society 2011, 133, 16786-16789.*
Mazzone, P. J. et al, Journal of Thoracic Oncology 2012, 7, 137-142.*
Polese, D. et al, Sensors and Actuators B 2013, 179 252-258.*
Chen, Q. et al, Sensors and Actuators B 2013, 183, 608-616.*
Lonsdale, C. L. et al, PLoS ONE 2013, 8, paper e62726, 10 pages.*
Broza, Y. Y. et al, Nanomedicine 2013, 8, 785-806.*
Askim, J. R. et al, Chemical Society Reviews 2013, 42, 8649-8682.*
Lim, S. H. et al, Journal of Clinical Microbiology 2014, 52, 592-598.*
Chen, Q. et al, LWT—Food Science and Technology 2014, 57, 502-507.*
Queralto, N. et al, Journal of Breath Research 2014, 8, paper 027112, 13 pages.*
Li, H. et al, Analytical Methods 2014, 6, 6271-6277.*
Xiaowei, H. et al, Meat Science 2014, 98, 203-210.*
Salinas, Y. et al, Food Control 2014, 35, 166-176 and 4 pages of supplementary material.*
Chen, Q. et al, Sensors and Actuators B 2014, 205, 1-8.*
Gu, H. et al., IEEE Sensors Journal 2014, 14, 2620-2625.*
Xiao-wei, H. et al, Food Chemistry 2014, 145, 549-554.*
Zaragoza, P. et al, Food Chemistry 2015, 175, 315-321.*
Dini, F. et al, Analytical and Bioanalytical Chemistry 2015, 407, 3975-3984 and pages of supplementary material.*
Basova, T. V. et al., Sensors and Actuators B 2015, 216, 204-211.*
Sun, W. et al, Talanta 2015, 143, 127-131.*
Urmila, H. et al, Analytical Methods 2015, 7, 5682-5688.*
Morsy, M. K. et al, Food Control 2016, 60, 346-352.*
Chen, Q. et al, Journal of Food Engineering 2016, 168, 259-266.*
Xiao-wei, H. et al, Food Chemistry 2016, 197, 930-936.*
Li, Z. et al, Analytical Chemistry 2016, 88, 5615-5620.*
Makote, R. et al, Analytica Chimica Acta 1999, 394, 195-200.*
Rottman, C. et al, Journal of the American Chemical Society 1999, 121, 8533-8543.*
Suslick, K. S. et al, Tetrahedron 2004, 60, 11133-11138.*
Kowada, Y. et al, Journal of Sol-Gel Science and Technology 2005, 33, 175-185.*
Zhang, C. et al, Journal of the American Chemical Society 2005, 127, 11548-11549.*
Zhang, C. et al, Journal of Agriculture and Food Chemistry 2007, 55, 237-242.*
Lim, S. H. et al, Analyst 2009, 134, 2453-2457.*
Soga, T.et al, Analytical Chemistry 2013, 85, 8973-8978.*
LaGasse, M. K. et al, Sensors and Actuators B 2014, 197, 116-122.*
Jang, M., Dissertation 2013, 173 pages.*
Li, Z. et al, Analyst 2015, 140, 5929-5935 and 26 pages of supplimentary information.*
Zhang, Y., Dissertation 2015, 187 pages.*
Askim et al., "Hand-Held Reader for Colorimetric Sensor Arrays," Anal. Chem. 2015, 87, 7810-7816.
Askin et al., "An optoelectronic nose for identification of explosives," Chem. Sci. 2016, 7, 199-206.
Chang and Lin, "LIBSVM: A Library for Support Vector Machines," ACM Trans. Intell. Syst. Technol. 2011, 2, 1-27.

* cited by examiner (i)

(ii)

(i)

(ii)

METHODS AND DEVICES FOR DETECTION OF TRIMETHYLAMINE (TMA) AND TRIMETHYLAMINE OXIDE (TMAO)

CROSS REFERENCE TO RELATED CASES

This is a non-provisional U.S. patent application that claims benefit of priority under 35 USC 119 to U.S. provisional application Ser. No. 62/338,063, filed May 18, 2016, and entitled "METHODS AND DEVICES FOR DETECTION OF TRIMETHYLAMINE (TMA)," the contents of which are herein incorporated by reference in its entirety.

STATEMENT REGARDING FEDERALLY SPONSORED RESEARCH OR DEVELOPMENT

This invention was made with government support under CHE1152232 awarded by National Science Foundation. The government has certain rights in the invention.

BACKGROUND

Trimethylaminuria (TMAU), also known as fish malodor syndrome, is a metabolic disorder characterized by excessive accumulation of the malodorous trimethylamine (TMA) in breath, sweat, and urine. TMAU is due to diminished activity of the flavin-containing monooxygenase-3 (FMO3) enzyme, which normally metabolizes TMA to the odorless trimethylamine N-oxide (TMAO). The prevalence of deficiency in FMO3 activity varies significantly among ethnic populations, ranging from <1% in the U.K. to 11% in New Guinea. As such, there is a pressing need for a highly sensitive and selective sensor for the medical diagnosis of trimethylaminuria and regular monitoring of TMA and TMAO concentrations during treatment.

A number of analytical methods have been applied to detect TMA, other biogenic amines or TMAO, including gas/high performance liquid chromatography, ion mobility spectrometry, quartz crystal microbalance and chemiresistive sensors (e.g., electronic nose techniques). Most of these methods, however, require expensive instrumentation, complicated preparation of the sensors, lack of portability, or long times for analysis.

Traditional electronic nose technology suffers from sensor drift, poor selectivity and environmental sensitivity (e.g., to changes in humidity or to interferents). The interactions between analytes and sensors are generally dominated by physical sorption or a single chemical interaction, which gives a limited dimensionality to the resulting data. For example, gas sensors based on the weak interaction between TMA and Co(II)-imidazolate framework or $\alpha$-$Fe_2O_3$/$TiO_2$ nanostructure can only reach detection limits of several ppm. Swager and coworkers have reported chemiresistive detectors made from Co porphyrin/carbon nanotube composites that exhibit sub-ppm sensitivity towards biogenic amines in 30 s. These sensors, however, cannot distinguish types of amines. A multidimensional sensor array based on various chemical properties therefore becomes essential to distinguish among various potential biomarkers for analytical purposes.

In comparison, colorimetric sensor arrays have a broad analyte response, good environmental tolerance, and high selectivity. In addition, they are also small, fast, disposable, and can be analyzed using inexpensive equipment. We have developed and improved an optoelectronic nose that uses colorimetric sensor arrays to detect and identify various analytes, ranging from toxic gases to beverages to microorganisms and even energetic materials, see Askim and Suslick, Anal. Chem. 2015, 87, 7810-7816 and WO 2015/034801. Application of colorimetric arrays to the detection of amines for meat spoilage has also been recently reported. Colorimetric sensor arrays rely on strong intermolecular interactions between the analytes and a chemically diverse set of cross-responsive dyes; the arrays use porous organically modified siloxanes (ormosils) or polymeric plasticizers to immobilize the chemically responsive colorants, whose UV-vis absorbances are altered by Brønsted and Lewis acid-base interactions, redox reactions, vapochromism/solvatochromism, etc.

We also report a new method for the detection and quantification of involatile TMAO by reduction of TMAO to TMA using sodium borohydride ($NaBH_4$) as reductant with Raney Nickel (RanNi) as catalyst. We have discovered that this reagent combination is effective in converting a TMAO solution that has been sparged or dried, thus removing any volatile amine components (e.g., free TMA), into a solution containing TMA in approximately the same amount as the initial involatile TMAO had been present. The newly formed TMA solution can be analyzed using the same colorimetric sensor array and thus quantify the initial concentration of TMAO in the solution before reduction.

SUMMARY OF THE INVENTION

In a first aspect, a method for detection and quantification of trimethylamine (TMA) and other volatile amines or derivatives of TMA is provided. The method includes two steps. The first step includes passing a sample over a sensor array comprising a substrate having a plurality of chemically responsive dyes selected from a group consisting of metal-containing dyes, pH indicators, and a solvatochromic/vapochromic dyes, or a combination thereof to produce changes in color in the sensor array. The second step includes detecting changes in color using an image sensor to determine the amount of TMA and other volatile amines or derivatives of TMA in the sample.

In a second aspect, a method for diagnosing trimethylaminuria (TMAU) in a subject is provided. The method includes two steps. The first step includes passing a sample from a subject over a sensor array comprising a substrate having a plurality of chemically responsive dyes or colorants selected from a group consisting of including metal-containing dyes, pH indicators, and a solvatochromic/vapochromic dyes to produce changes in color in the sensor array. The second step includes detecting changes in color using an image sensor to determine the amount of TMA or derivatives of TMA in the sample. The presence of TMA or derivatives of TMA detected in the sample above a predetermined concentration range is indicative of a positive diagnosis of a patient having TMAU.

In a third aspect, a sensor array for detection of TMA is provided. The sensor array includes a substrate having a plurality of chemically responsive dyes or colorants selected from a group consisting of a metal-containing dye, a pH indicator, and a solvatochromic dye.

In a fourth aspect, a device for detection of TMA is provided. The device includes three elements. The first element includes a linear array of optically-responsive chemical sensing elements comprising a plurality of chemically responsive dyes or colorants selected from a group consisting of a metal-containing dye, a pH indicator, and a solvatochromic dye. The second element includes an image sensor in optical communication with the linear array for determining a spectral response of the optically-responsive chemical sensing elements, the image sensor comprising at least one light emission source. The third element includes electronics in electrical communication with the image sensor. The electronics is configured with a non-transitory tangible computer readable medium having computer readable program code for analyzing spectral response data.

In a fifth aspect, a device for quantifying trimethylamine (TMA) and trimethylamine oxide (TMAO) is provided. The device includes several elements. The first element includes a colorimetric sensor array. The second element includes an imaging device. The third element includes an electronic device configured with a non-transitory tangible computer readable medium having computer readable program code for analyzing spectral response data. The imaging device is configured in optical communication with the colorimetric sensor array and in electrical communication with the electronic device.

In a sixth aspect, a method for the quantification of involatile TMAO by the initial removal of volatile amines, including TMA, is provided. The method includes several steps. The first step includes air or other gas sparging or evaporation of a liquid sample to produce a residue. The second step includes re-dissolution of the residue in an aqueous solution to form a reconstituted sample. The third step includes reducing TMAO to TMA in the reconstituted sample. The fourth step includes analyzing the volatile TMA so produced.

These and other features, objects and advantages of the present invention will become better understood from the description that follows. In the description, reference is made to the accompanying drawings, which form a part hereof and in which there is shown by way of illustration, not limitation, of the embodiments of the invention.

BRIEF DESCRIPTION OF THE DRAWINGS

The features, objects and advantages other than those set forth above will become more readily apparent when consideration is given to the detailed description below. Such detailed description makes reference to the following drawings.

starting concentration of TMAO was 200 µM and the amount of Raney Ni is 0.1 mg/mL.

Figure 23:
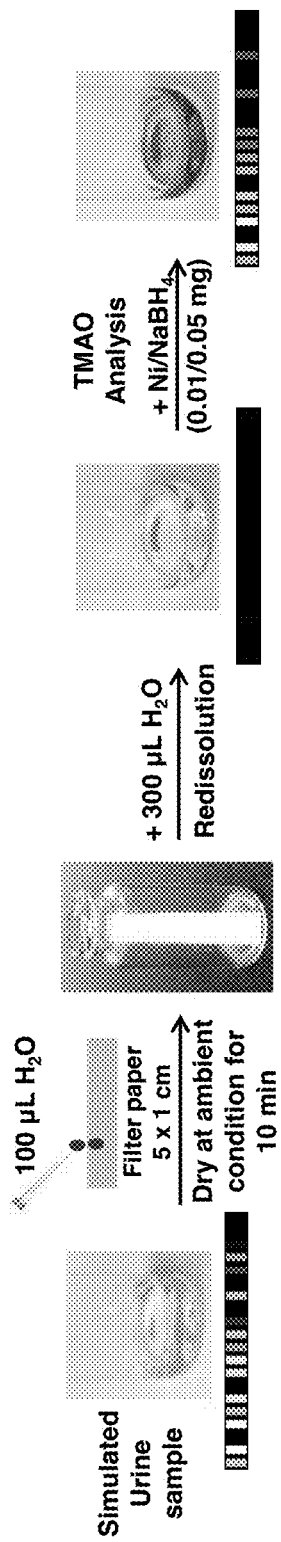

FIG. 23 depicts the sequence of wetting a piece of filter paper with a liquid sample containing volatile amines and TMAO (e.g., a urine sample), allowing the volatiles to evaporate, re-dissolving the non-volatile compounds that remain, reducing the TMAO to TMA and then finally analyzing the volatile TMA so formed.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

The patent or application file contains at least one drawing executed in color. Copies of this patent or patent application publication with color drawing(s) will be provided by the Office upon request and payment of the necessary fee.

DETAILED DESCRIPTION

The methods and devices now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Likewise, many modifications and other embodiments of the methods and devices described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Overview

The present disclosure provides an inexpensive and sensitive colorimetric method for rapid detection of gaseous and aqueous TMA as well as a rapid method for the conversion of TMAO to TMA and quantification of TMAO from the TMA so produced. Both TMA and TMAO are metabolites related to trimethylaminuria (TMAU), also known as fish malodor syndrome. Three main classes of colorants were incorporated in a colorimetric sensor array (shown in FIG. 1A): (1) metal-containing dyes (e.g., Zn(II) metalloporphyrin) that respond to Lewis basicity to simulate mammalian olfactory receptors; (2) pH indicators that respond to Brønsted basicity; (3) dyes with large permanent dipoles (solvatochromic dyes, e.g., vapochromic dyes) that respond to local polarity. In one embodiment, twenty sensor array elements (e.g., spots) were rigorously optimized in their formulations by adjusting the dye amount and pH to enhance their sensitivity (Table 1, FIG. 1A). The use of highly porous sol-gel formulations were used to obtain a better responsiveness to gaseous analytes, as well as for the ideal hydrophobicity of the matrix to minimize the dissolution of the dyes during liquid sensing.

The present disclosure also provides simple and portable colorimetric sensor arrays and devices for the detection of trimethylamine (TMA) and TMA derivatives (e.g., TMAO, ammonia, methylamine, dimethylamine, etc.) from vapor or aqueous solution (FIG. 1B) using various imaging devices with relevance to point of care diagnosis of a genetic and metabolic disease, trimethylaminuria (TMAU). Apparent color differences shown by the sensor arrays allow for a quick identification of TMA concentrations even without imaging devices. LODs for trimethylamine in the gas phase are a few ppb and in aqueous phase a few µM (FIGS. 2A and 2B), which are well below the diagnostically significant concentration for TMAU. We have examined new methods for portable acquisition of colorimetric data and importantly, and made comparisons between them (e.g., flat bed scanner vs. cell phone camera vs. customized line scanner handheld imagers as seen in FIGS. 8, 6 and 5A-B). Principal component analysis (FIGS. 4A-B), hierarchical cluster analysis (FIGS. 3 and 6) and support vector machine analysis all show excellent discriminatory power over a wide range of concentrations for three different imaging methods (including cell phone camera) with error rates <1%. The sensor array is robust and reusable after multiple exposures (FIGS. 11A-B), but its preferred embodiment is as a disposable sensor array. The optoelectronic nose promises to be a useful point of care device for rapid, quantitative diagnosis and monitoring of trimethylamine levels for patients with trimethylaminuria, and for the detection of spoiling of foods and food sources (e.g., fish, meats, poultry).

We have also designed an effective reductant and catalyst (e.g., $NaBH_4$ with Raney Nickel) for the rapid conversion of TMAO to TMA, which enables the analysis of the less basic and involatile TMAO. This extends the use of the optoelectronic nose as a useful point of care device for rapid, quantitative diagnosis and monitoring of trimethylaminoxide (TMAO) levels for patients with trimethylaminuria or other metabolic defects related to conversion of amines into amine-N-oxides.

Figure 1A:
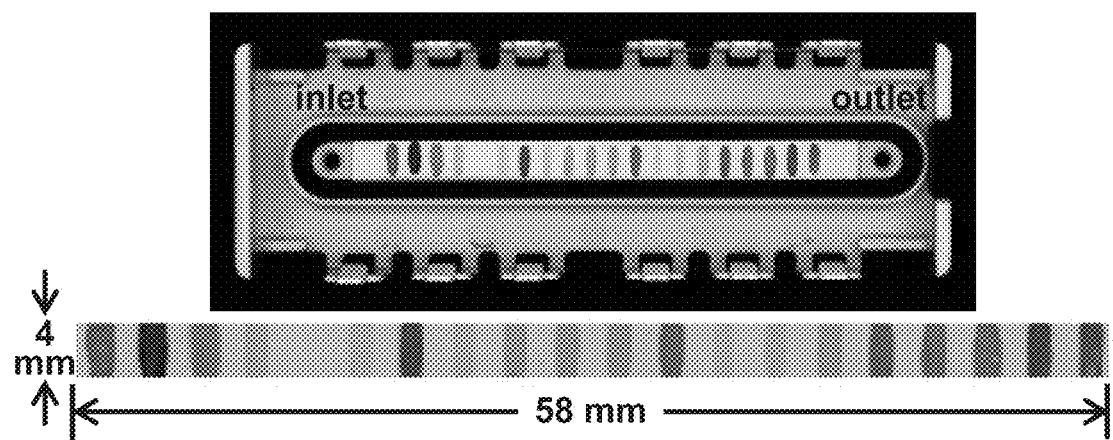
FIG. 1A depicts an exemplary embodiment of a colorimetric sensor array for TMA detection that includes a linearized 20-element sensor array for vapor detection, wherein the array mounted on a polycarbonate cartridge with an o-ring placed in a groove and a glass slide cover in place, which provides an ideal flow path for analytes and a flow volume of <180 μL (77×4.5×0.5 mm).
Figure 1B:
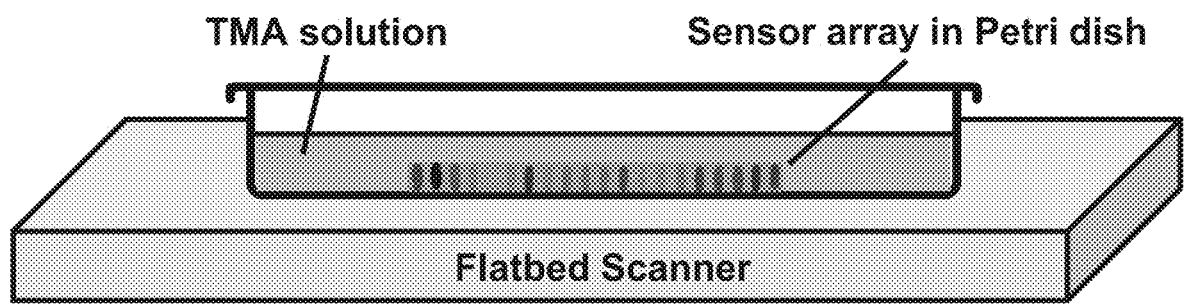
FIG. 1B depicts a schematic of an exemplary experimental set-up having a closed Petri dish containing 10 mL of a buffered TMA aqueous solution, an array positioned in the solution, and an ordinary flatbed scanner for imaging.

In one embodiment, the chemically responsive dyes are Ethanone+TsOH, α-Naphthyl Red+TsOH, 5,10,15,20-tetrakis(2,4,6-trimethylphenyl) porphyrinatozinc(II), Tetraiodophenolsulfonephthalein, Fluorescein, Bromocresol Green, Methyl Red, Bromocresol Purple, Bromophenol Red, Rosolic Acid, Bromopyrogallol Red, Pyrocatechol Violet, 4-[2-[4-(dimethylamino)phenyl]ethenyl]-2,6-dimethylpyrylium, $LiNO_3$+Cresol Red, $Pb(OAc)_2$+Disperse Red, $AgNo_3$+Bromophenol Blue, $AgNO_3$+Bromocresol Green, $Zn(OAc)_2$+m-Cresol Purple+TBAH, $HgCl_2$+Bromophenol Blue+TBAH, and $HgCl_2$+Bromocresol Green+TBAH, as shown in FIG. 1A and Table 1.

TABLE 1

Sensor spot compositions of the colorimetric sensor array.

| Spot # | Name | mg |
|---|---|---|
| 1 | Ethanone + TsOH | 2/10 µL |
| 2 | α-Naphthyl Red + TsOH | 4/20 µL |

TABLE 1-continued

Sensor spot compositions of the colorimetric sensor array.

| Spot # | Name | mg |
|---|---|---|
| 3 | 5,10,15,20-tetrakis(2,4,6-trimethylphenyl)porphyrinatozinc(II) | 4.0 |
| 4 | Tetraiodophenolsulfonephthalein | 4.0 |
| 5 | Fluorescein | 2.0 |
| 6 | Bromocresol Green | 4.0 |
| 7 | Methyl Red | 4.0 |
| 8 | Bromocresol Purple | 4.0 |
| 9 | Bromophenol Red | 4.0 |
| 10 | Rosolic Acid | 4.0 |
| 11 | Bromopyrogallol Red | 2.0 |
| 12 | Pyrocatechol Violet | 4.0 |
| 13 | 4-[2-[4-(dimethylamino)phenyl]ethenyl]-2,6-dimethylpyrylium | 2.0 |
| 14 | $LiNO_3$ + Cresol Red | 15/4 |
| 15 | $Pb(OAc)_2$ + Disperse Red | 15/0.5 |
| 16 | $AgNO_3$ + Bromophenol Blue | 5.0/2.0 |
| 17 | $AgNO_3$ + Bromophenol Green | 5.0/2.0 |
| 18 | $Zn(OAc)_2$ + m-Cresol Purple + TBAH | 20/4/50 μL |
| 19 | $HgCl_2$ + Bromophenol Blue + TBAH | 5.0/4.0/50 μL |
| 20 | $HgCl_2$ + Bromophenol Green + TBAH | 5.0/4.0/50 μL |

TBAH: 1.0M in 2-MeOEtOH
TsOH: 1.0M in 2-MeOEtOH

Figure 5A:
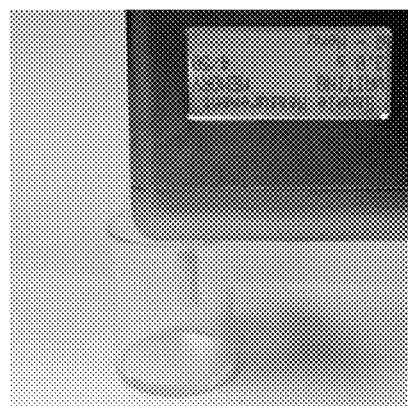
FIG. 5A depicts an exemplary experimental set-up for mouth odor simulation using the handheld device, wherein headspace gas was sampled from 2 mL TMA solution in the beaker for a mouth odor test (panel (i)) to generate an averaged sensor array response to different concentrations of TMA and controls (healthy controls were collected from an inventor) (panel (ii)). Each sample was collected in septuplicate. For display purposes, S/N ratios of 3-10 were scaled on an 8-bit RGB color scale (i.e., 0-255).
Figure 5A:
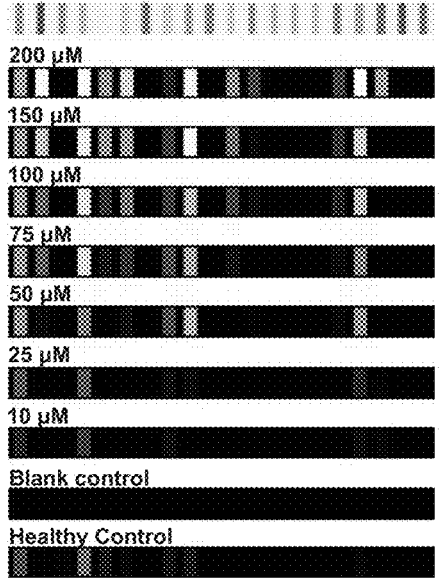
Figure 5B:
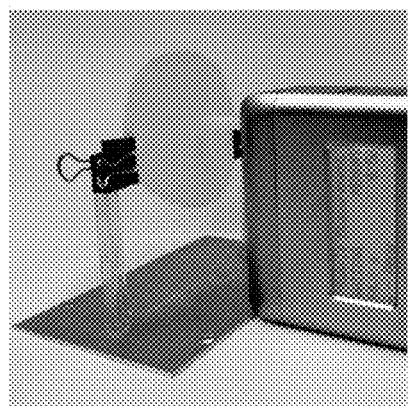
FIG. 5B depicts an exemplary experimental set-up for skin odor simulation using the handheld device, wherein filter paper was soaked in 0.5 mL TMA solution for the skin odor test (panel (i)) to generate an averaged sensor array response to different concentrations of TMA and controls (healthy controls were collected from the axilla of an inventor) (panel (ii)). Each sample was collected in septuplicate. For display purposes, S/N ratios of 3-10 were scaled on an 8-bit RGB color scale (i.e., 0-255).
Figure 5B:
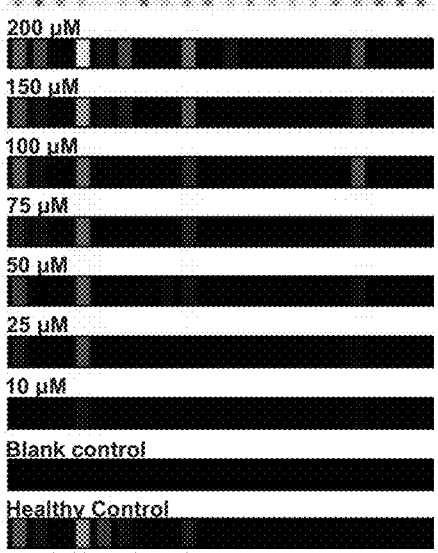
Figure 6:
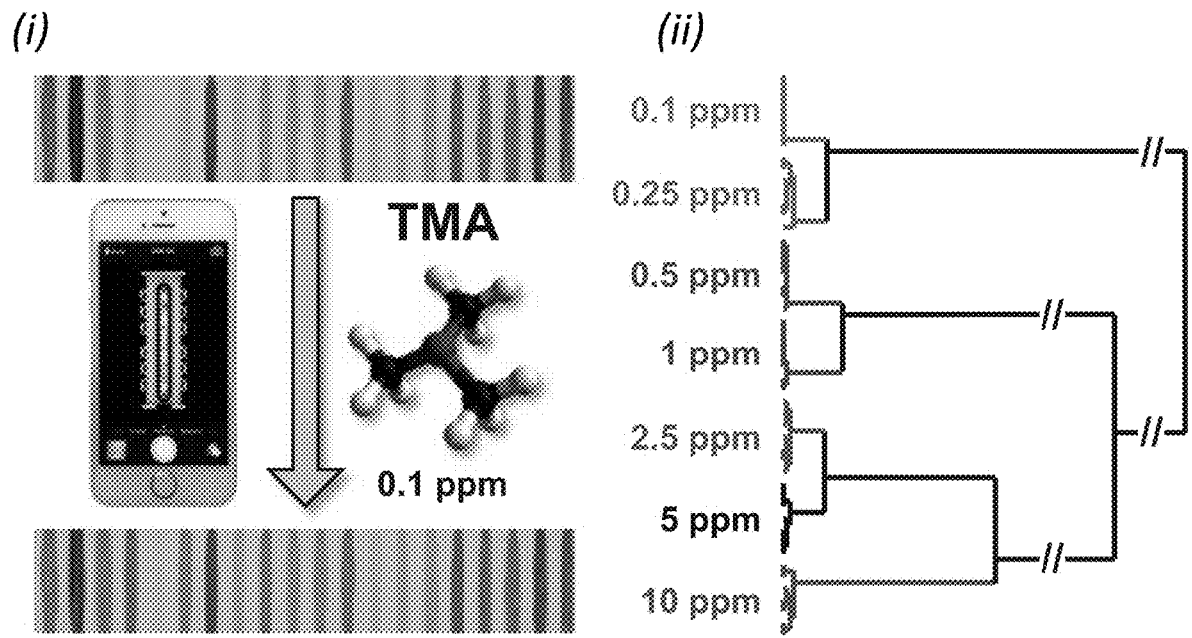
FIG. 6 illustrates an exemplary schematic of TMA detection with a cell phone device (panel (i)) and a resultant exemplary depiction of detection response with a total array response being represented by the total Euclidean distance of the dimensional color difference vector (panel (ii)).

As used herein, the term "sample" is used herein in its broadest sense. A sample may be a biological sample obtained from a subject (e.g., a human) or from components (e.g., tissues) of a subject. The sample may be of any biological tissue or fluid with which TMA or TMAO may be assayed. Frequently, the sample will be a "clinical sample", i.e., a sample derived from a patient. Such samples include, but are not limited to, bodily fluids, e.g., urine, blood, sweat blood plasma, vitreous or aqueous humor fluid, saliva; tissue or fine needle biopsy samples; and archival samples with known diagnosis, treatment and/or outcome history. The term sample also encompasses any material derived by processing the biological sample. Derived materials include, but are not limited to, cells (or their progeny) isolated from the sample, proteins or nucleic acid molecules extracted from the sample. Processing of the sample may involve one or more of, filtration, distillation, extraction, concentration, inactivation of interfering components, addition of reagents, and the like. The sample may also be the breath from a subject subject, or air in close proximity to the subject. In a preferred embodiment, the sample is sweat, urine, saliva, breath from a subject, or air located in the vicinity of the subject (e.g., close to the skin), as shown in FIGS. 5A-B.

The sample may also be air from a particular container, room, area of interest, or air in close proximity to food sources, such as meats (e.g., fish). The methods described herein may also be useful for detecting the presence of TMA and derivatives of TMA in a room or a particular area to be able to detect rotting meats (e.g., fish). The air may be forcefully passed over the sensor arrays by mechanical blowing or sucking. In another embodiment, the sample may be air from a container or air in close proximity to the food source (e.g., fish). The detection of TMA and TMA derivatives is also useful for determining the level of spoiling of the meat.

By "test object" it is meant any source where the detection of TMA or TMA derivatives is desired. The test object can be, for example, a particular room, and particular area, a food container, a food source, the area surrounding a food source, a food transport vehicle, and the like.

The term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The term "image sensor" includes anything capable of reading the changes in color of the chemically responsive dyes, including, but not limited to, a flatbed scanner, a cell phone camera, a digital camera, a hand-held device, a camera connected to a computer, and the naked eye.

The term "predetermined concentration range," as used in reference to a method for diagnosing trimethylaminuria (TMAU) in a subject, refers to the range of concentrations of a given analyte present in a normal, healthy subject or patient not having TMAU.

The terms "sensor array" and "colorimetric sensor array" have the same meaning as used herein and refer generally to a substrate having a plurality of chemically responsive dyes or colorants deposited thereon. An example of this technology may be found in U.S. Patent Application Publication U.S. 2010-0166604 A1, "COLORIMETRIC SENSOR ARRAYS BASED ON NANOPOROUS PIGMENTS" to Sung H. Lim et al., the contents of which are hereby incorporated by reference in its entirety.

APPLICATIONS

In a first aspect, a method for detection and quantification of trimethylamine (TMA) and other volatile amines or derivatives of TMA is provided. The method includes two steps. The first step includes passing a sample over a sensor array comprising a substrate having a plurality of chemically responsive dyes or colorants selected from a group consisting of metal-containing dyes, pH indicators, and a solvatochromic/vapochromic dyes, or a combination thereof to produce changes in color in the sensor array. The second step includes detecting changes in color using an image sensor to determine the amount of TMA and other volatile amines or derivatives of TMA in the sample.

In a first respect, the plurality of chemically responsive dyes or colorants is selected form a group consisting of Ethanone+TsOH, α-Naphthyl Red+TsOH, 5,10,15,20-tetrakis(2,4,6-trimethylphenyl)porphyrinatozinc(II), Tetraiodophenolsulfonephthalein, Fluorescein, Bromocresol Green, Methyl Red, Bromocresol Purple, Bromophenol Red, Rosolic Acid, Bromopyrogallol Red, Pyrocatechol Violet, 4-[2-[4-(dimethylamino)phenyl]ethenyl]-2,6-dimethylpyrylium, $LiNO_3$+Cresol Red, $Pb(OAc)_2$+Disperse Red, $AgNo_3$+Bromophenol Blue, $AgNO_3$+Bromocresol Green, $Zn(OAc)_2$+m-Cresol Purple+TBAH, $HgCl_2$+Bromophenol Blue+TBAH, and $HgCl_2$+Bromocresol Green+TBAH. In a second respect, the plurality of chemically responsive dyes or colorants are present in the amounts shown in Table 1. In a third respect, the sample is selected from a group consisting of sweat, saliva, urine, vapor from breath, air blown in from the surrounding area, water vapor, air from a room or area to be tested, air in proximity to a test subject, and air in proximity to a test object. In a fourth respect, the plurality of chemically responsive dyes or colorants are arranged in a linear array. In a fifth respect, the plurality of chemically responsive dyes or colorants is selected from a group of metal-containing dyes responding to Lewis basicity, the pH indicators responding to Bronsted basicity, and the solvatochromic dyes responding to local polarity. In a sixth respect the image sensor is selected from a hand-held device, a cell phone, a flatbed scanner and a computer-connected imaging device. In a seventh respect, the substrate comprises a highly porous sol-gel formulation.

In a second aspect, a method for diagnosing trimethylaminuria (TMAU) in a subject is provided. The method includes two steps. The first step includes passing a sample from a subject over a sensor array comprising a substrate having a plurality of chemically responsive dyes or colorants selected from a group consisting of including metal-containing dyes, pH indicators, and a solvatochromic/vapochromic dyes to produce changes in color in the sensor array. The second step includes detecting changes in color using an image sensor to determine the amount of TMA or derivatives of TMA in the sample. The presence of TMA or derivatives of TMA detected in the sample above a predetermined concentration range is indicative of a positive diagnosis of a patient having TMAU.

In a third aspect, a sensor array for detection of TMA is provided. The sensor array includes a substrate having a plurality of chemically responsive dyes or colorants selected from a group consisting of a metal-containing dye, a pH indicator, and a solvatochromic dye.

In a first respect of the third aspect, the plurality of chemically responsive dyes or colorants are selected from a group consisting of Ethanone+TsOH, α-Naphthyl Red+TsOH, 5,10,15,20-tetrakis(2,4,6-trimethylphenyl)porphyrinatozinc(II), Tetraiodophenolsulfonephthalein, Fluorescein, Bromocresol Green, Methyl Red, Bromocresol Purple, Bromophenol Red, Rosolic Acid, Bromopyrogallol Red, Pyrocatechol Violet, 4-[2-[4-(dimethylamino)phenyl]ethenyl]-2,6-dimethylpyrylium, $LiNO_3$+Cresol Red, $Pb(OAc)_2$+Disperse Red, $AgNo_3$+Bromophenol Blue, $AgNO_3$+Bromocresol Green, $Zn(OAc)_2$+m-Cresol Purple+TBAH, $HgCl_2$+Bromophenol Blue+TBAH, and $HgCl_2$+Bromocresol Green+TBAH. In a second respect of the third aspect, the sensor array is a disposable cartridge. In a third respect of the third aspect, the sensor array is included in a device for detection of TMA. Additional elements of the device include an image sensor in optical communication with the sensor array for determining a spectral response of the optically-responsive chemical sensing elements, the image sensor comprising at least one light emission source and electronics in electrical communication with the image sensor. The electronics is configured with a non-transitory tangible computer readable medium having computer readable program code for analyzing spectral response data. An exemplary transitory tangible computer readable medium having computer readable program code for this purpose includes a customized software package, SpotFinder 1.0.6 (iSense LLC., Mountain View, Calif.).

In a fourth aspect, a device for detection of TMA is provided. The device includes three elements. The first element includes a linear array of optically-responsive chemical sensing elements comprising a plurality of chemically responsive dyes or colorants selected from a group consisting of a metal-containing dye, a pH indicator, and a solvatochromic dye. The second element includes an image sensor in optical communication with the linear array for determining a spectral response of the optically-responsive chemical sensing elements, the image sensor comprising at least one light emission source. The third element includes electronics in electrical communication with the image sensor. The electronics is configured with a non-transitory tangible computer readable medium having computer readable program code for analyzing spectral response data. An exemplary transitory tangible computer readable medium having computer readable program code for this purpose includes a customized software package, SpotFinder 1.0.6 (iSense LLC., Mountain View, Calif.).

In a first respect of the fourth aspect, the linear array is configured in a disposable cartridge. In a second respect of the fourth aspect, the plurality of chemically responsive dyes or colorants is selected from a group consisting of Ethanone+TsOH, π-Naphthyl Red+TsOH, 5,10,15,20-tetrakis(2,4,6-trimethylphenyl)porphyrinatozinc(II), Tetraiodophenolsulfonephthalein, Fluorescein, Bromocresol Green, Methyl Red, Bromocresol Purple, Bromophenol Red, Rosolic Acid, Bromopyrogallol Red, Pyrocatechol Violet, 4-[2-[4-(dimethylamino)phenyl]ethenyl]-2,6-dimethylpyrylium, $LiNO_3$+Cresol Red, $Pb(OAc)_2$+Disperse Red, $AgNo_3$+Bromophenol Blue, $AgNO_3$+Bromocresol Green, $Zn(OAc)_2$+m-Cresol Purple+TBAH, $HgCl_2$+Bromophenol Blue+TBAH, and $HgCl_2$+Bromocresol Green+TBAH.

In a fifth aspect, a device for quantifying trimethylamine (TMA) and trimethylamine oxide (TMAO) is provided. The device includes several elements. The first element includes a colorimetric sensor array. The second element includes an imaging device. The third element includes an electronic device configured with a non-transitory tangible computer readable medium having computer readable program code for analyzing spectral response data. An exemplary transitory tangible computer readable medium having computer readable program code for this purpose includes a customized software package, SpotFinder 1.0.6 (iSense LLC., Mountain View, Calif.). The imaging device is configured in optical communication with the colorimetric sensor array and in electrical communication with the electronic device In a first respect of the fifth aspect, the imaging device is selected from a group consisting of a flatbed scanner, a digital camera, a CMOS (complementary metal-oxide-semiconductor) imaging sensor, a CCD (charge coupled device) imaging sensor, and a CIS (contact image sensor). In a second respect of the fifth aspect, the electronic device is selected from a group consisting of a computer, a cell phone and a handheld reader.

In a sixth aspect, a method for the quantification of involatile TMAO by the initial removal of volatile amines, including TMAO, is provided. The method includes several steps. The first step includes air or other gas sparging or evaporation of a liquid sample to produce a residue. The second step includes re-dissolution of the residue in an aqueous solution to form a reconstituted sample. The third step includes reducing TMAO to TMA in the reconstituted sample. The fourth step includes analyzing the volatile TMA so produced.

In a first respect of the sixth aspect, the step of reducing TMAO comprising use of a reductant being selected from a group consisting of sodium borohydride, or other related derivatives including salts of cyanoborohydride or triethylborohydride or tri-isopropylborohydride, lithium aluminum hydride, sodium bis(2-methoxyethoxy)aluminum hydride (Red-Al) and diiso-butylaluminum hydride (Dibal-H). In this respect, the use of a reductant occurs in the presence of a transition metal catalyst, Raney Nickel, platinum, palladium as nanoparticles or colloids or supported on supports such as alumina, silica, or activated carbon.

EXAMPLES

Example 1

Methods and Devices for TMA Analysis

Figure 2A:
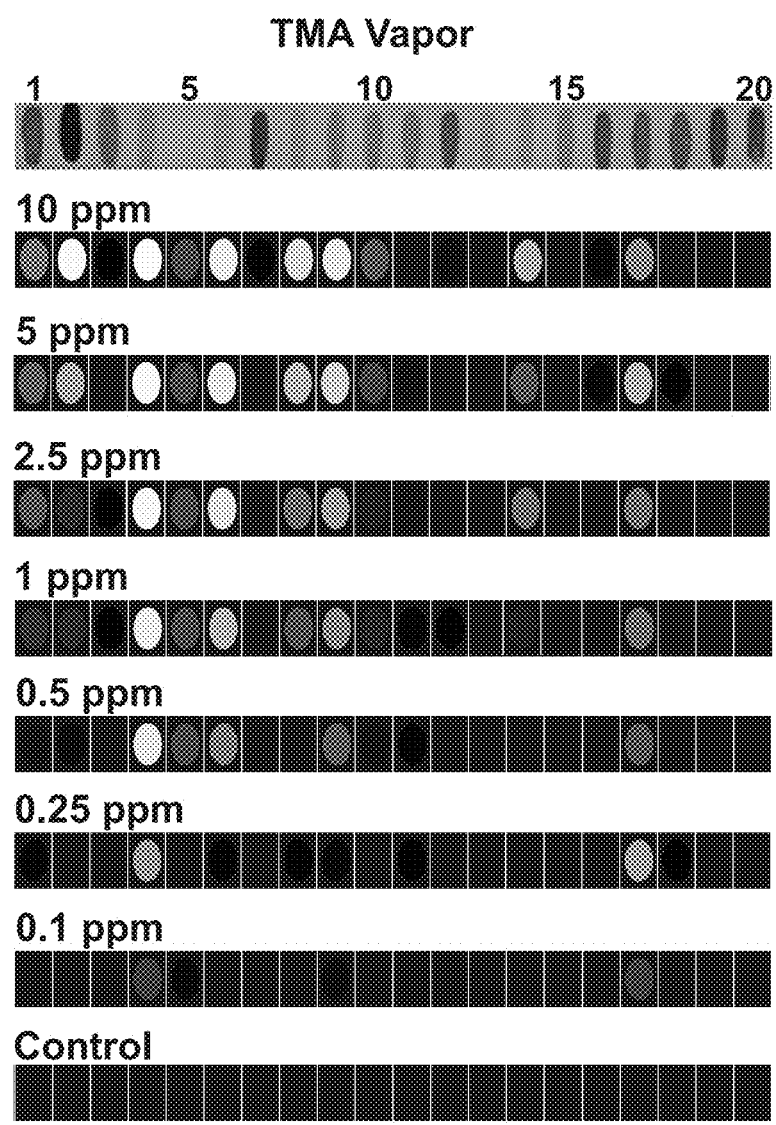
FIG. 2A Average responses of the sensor array to different concentrations of gaseous TMA and controls, each run in septuplicate trials. For visualization, the color range is expanded from 4 to 8 bits per color (i.e., RGB color range of 4-19 expanded to 0-255).
Figure 2B:
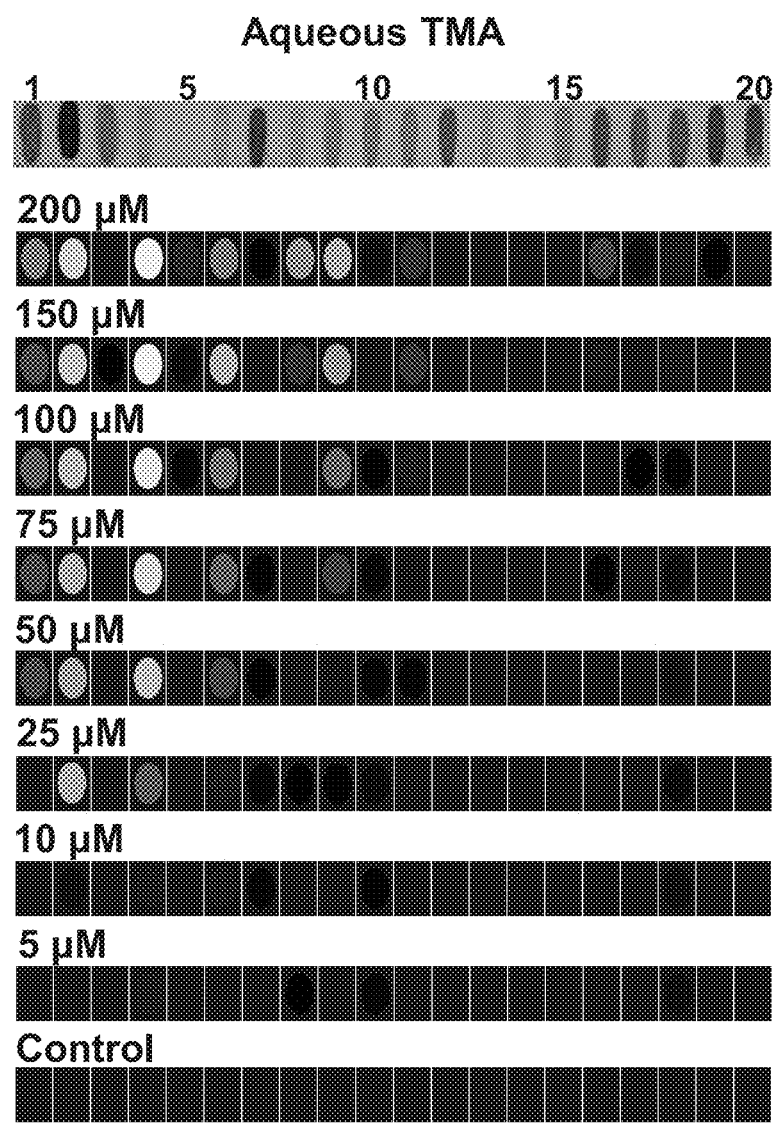
FIG. 2B depicts average responses of the sensor array to different concentrations of aqueous TMA and controls, each run in septuplicate trials. For visualization, the color range is expanded from 4 to 8 bits per color (i.e., RGB color range of 4-19 expanded to 0-255).
Figure 7A:
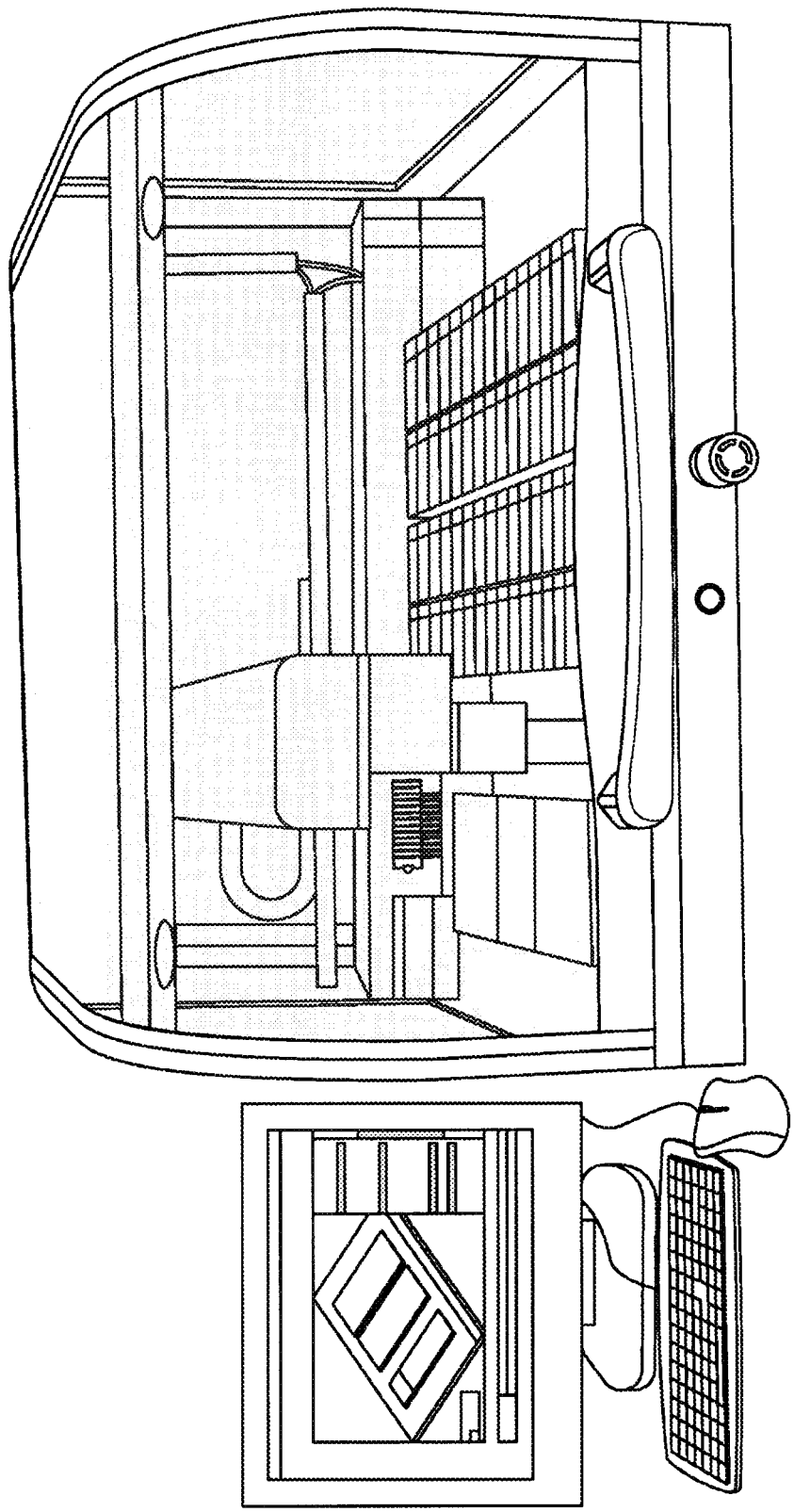
FIG. 7A depicts an exemplary embodiment of a printer (NanoPrint robotic pin printer, Array-It, Inc. (Sunnyvale, Calif., USA) used to print array cartridges.
Figure 7B:
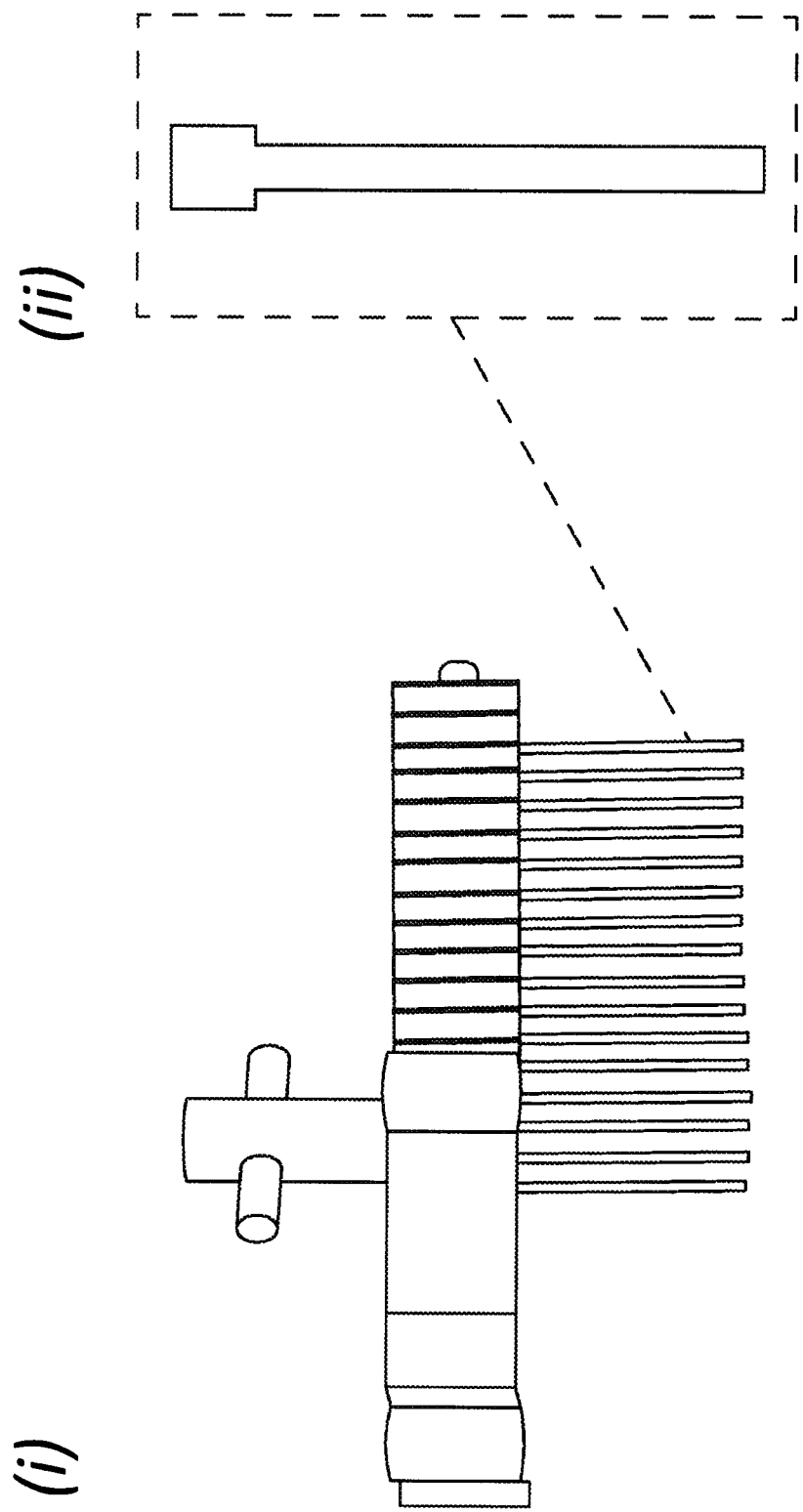
FIG. 7B illustrates an exemplary rectangular pin-holder (panel (i)) and pins for printing on the exemplary printer of FIG. 7A (panel (ii)).
Figure 8:
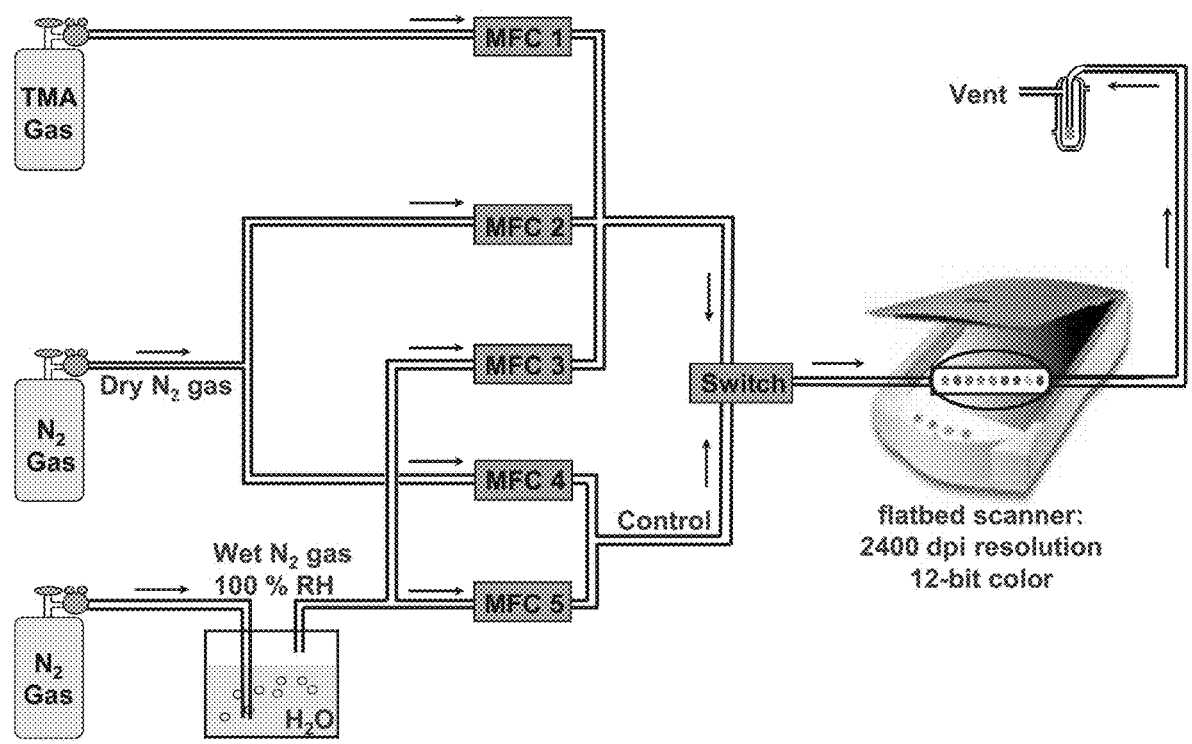
FIG. 8 depicts an exemplary gas mixing apparatus for exposure of sensor array to gaseous TMA. MFC=mass flow controller.
Figure 9:
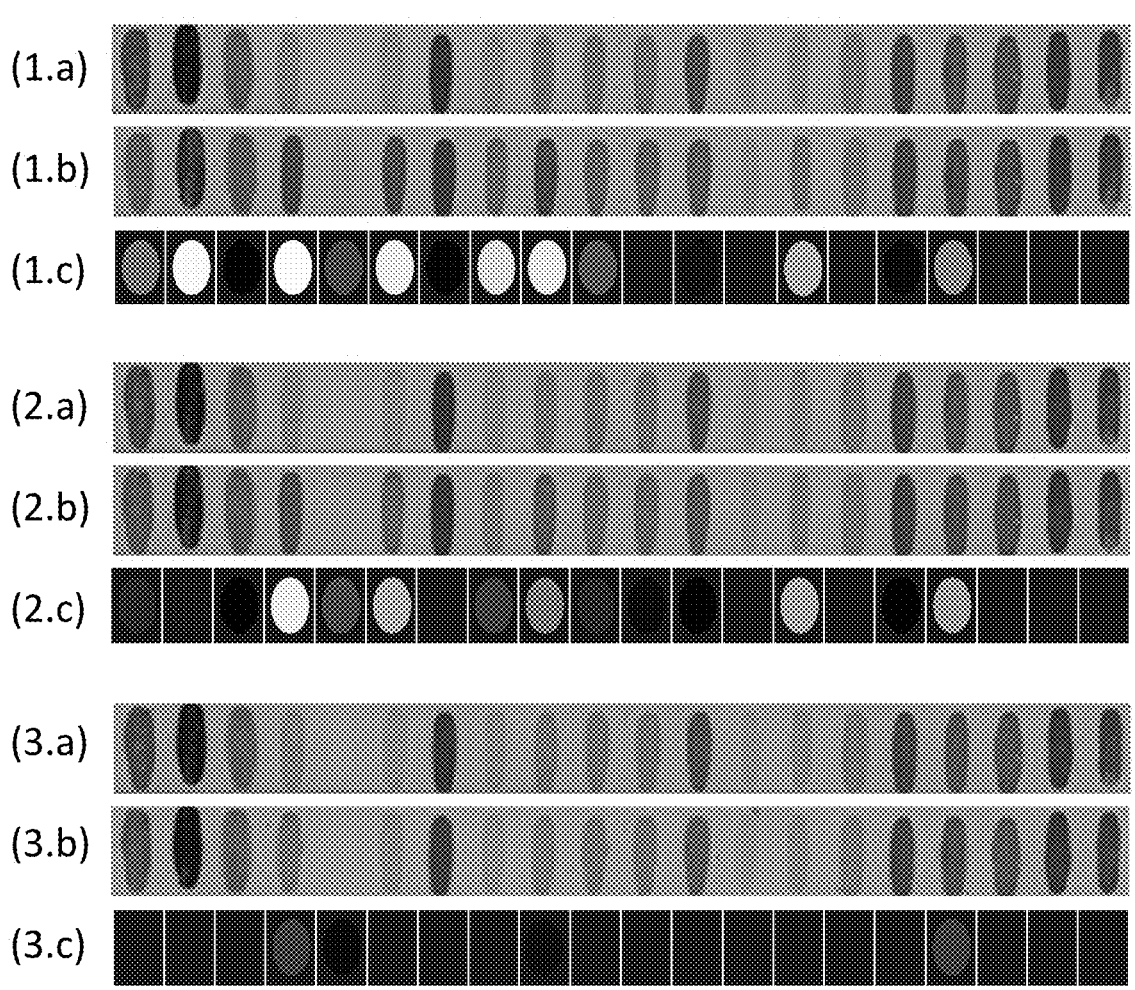
FIG. 9 depicts representative images before exposure to 10 ppm, 1 ppm and 0.1 ppm TMA, respectively (panels (1.a), (2.a) and (3.a), respectively), after 2 minute exposure to 10 ppm, 1 ppm and 0.1 ppm TMA, respectively (panels (1.b), (2.b) and (3.b), respectively) and the resultant color difference images as a result of exposure to 10 ppm, 1 ppm and 0.1 ppm TMA, respectively (panels (1.c), (2.c) and (3.c), respectively). For visualization, the color difference images are shown for a color range expanded from 4 bits (4-19) to 8 bits (0-255).
Figure 10A:
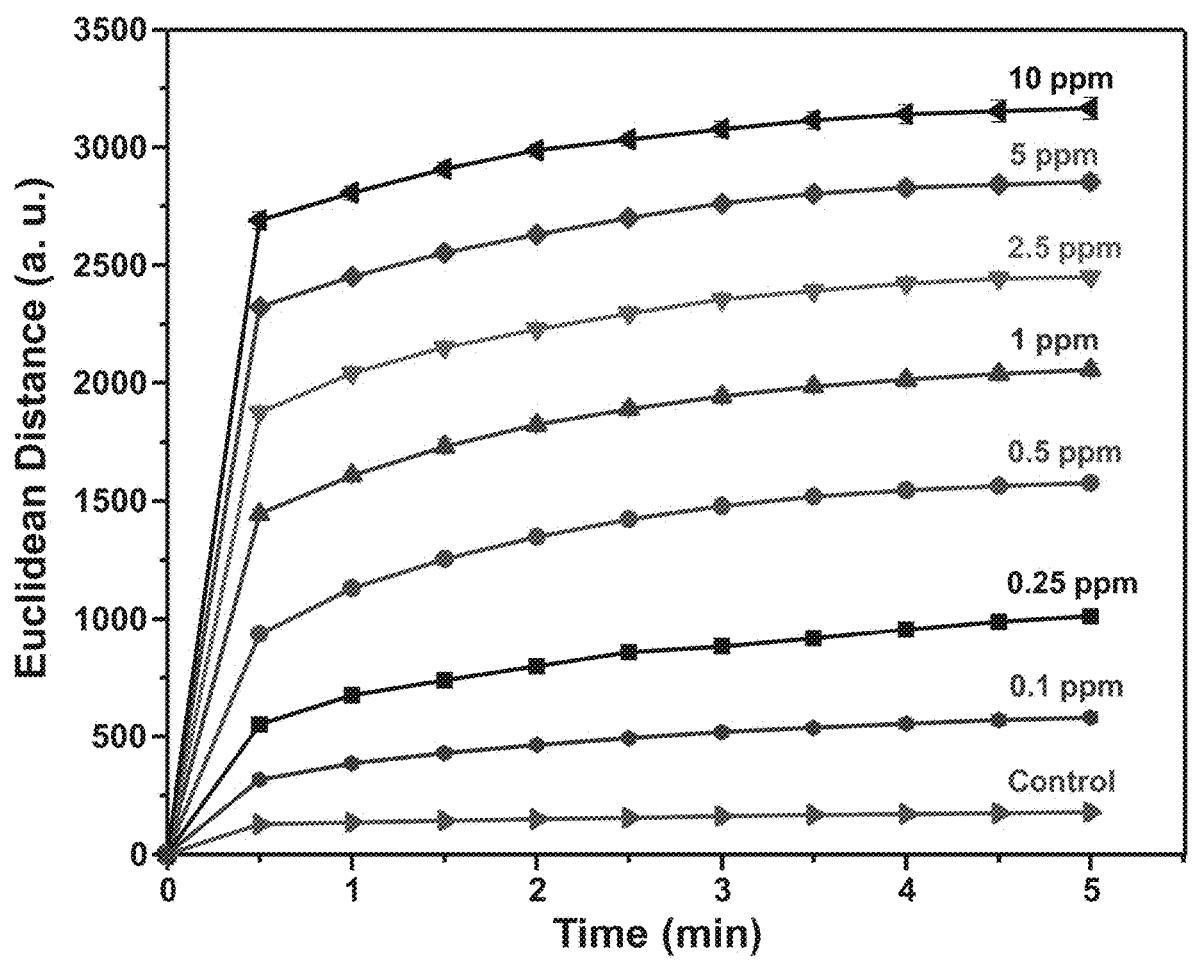
FIG. 10A depicts Array response curves of gaseous TMA concentrations as a function of time. The average value with error bars set to 2 σ from septuplicate trials is shown. Total Euclidean distance is the total length of the color difference vector, i.e., the total array response, defined as the square root of the sum of the squares of the changes in RGB values of all 60 dimensions. The average value with error bars set to 2 σ from septuplicate trials for each concentration is shown.
Figure 10B:
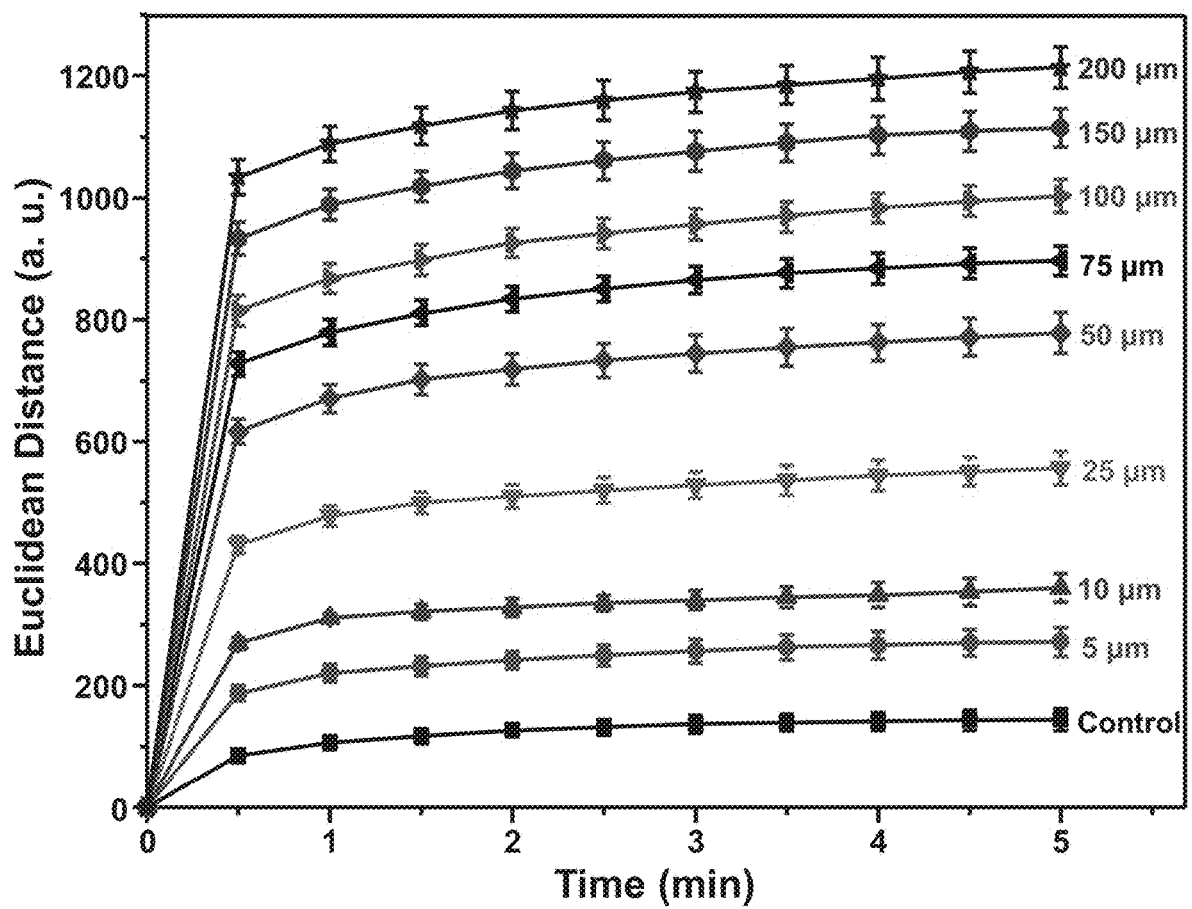
FIG. 10B depicts array response curves of aqueous TMA concentrations as a function of time. The average value with error bars set to 2 σ from septuplicate trials is shown. Total Euclidean distance is the total length of the color difference vector, i.e., the total array response, defined as the square root of the sum of the squares of the changes in RGB values of all 60 dimensions. The average value with error bars set to 2 σ from septuplicate trials for each concentration is shown.
Figure 11A:
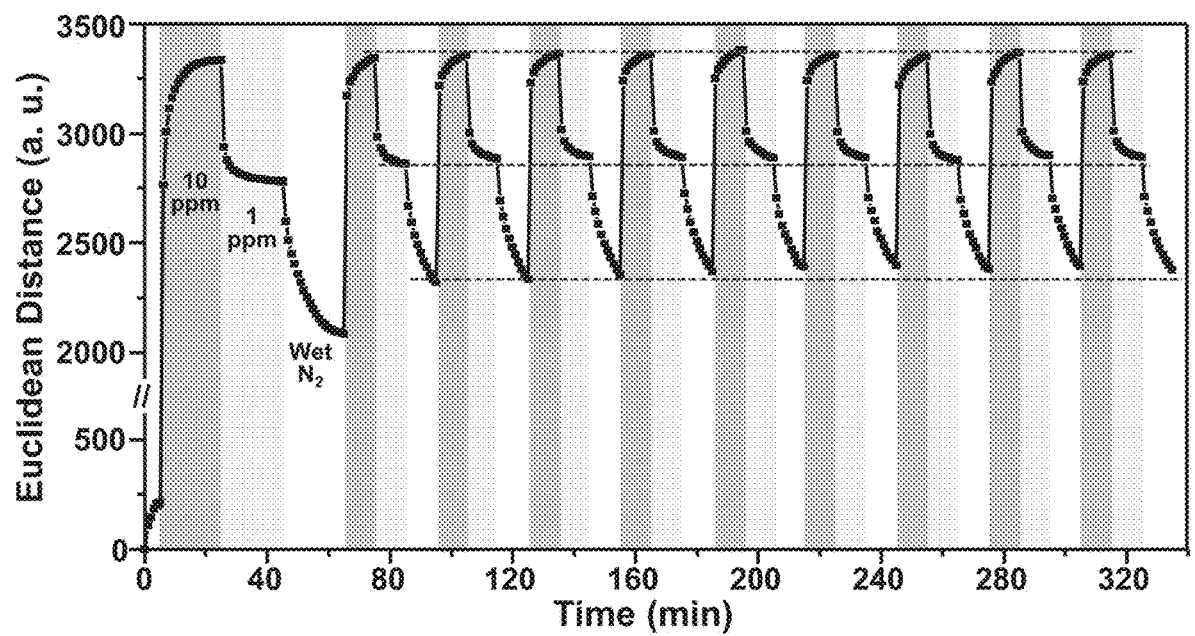
FIG. 11A illustrates the reversibility of sensor array response during 10 rounds of cycling for gaseous TMA exposure of a single array from nitrogen to 10 ppm, and then repeatedly from 10 ppm to 1 ppm and back to the background (i.e., nitrogen at 50% relatively humidity). Data were acquired every 1 min; total response duration is 335 min; the total array response is represented by the total Euclidean distance of the 60-dimensional color difference vector. 90% of complete equilibration is achieved within 2 min of the first exposure to 10 ppm TMA and within 3 min for subsequent cycling between 10 and 1 ppm exposures. The blue lines are horizontal showing the lack of drift over 10 rounds of cycling.
Figure 11B:
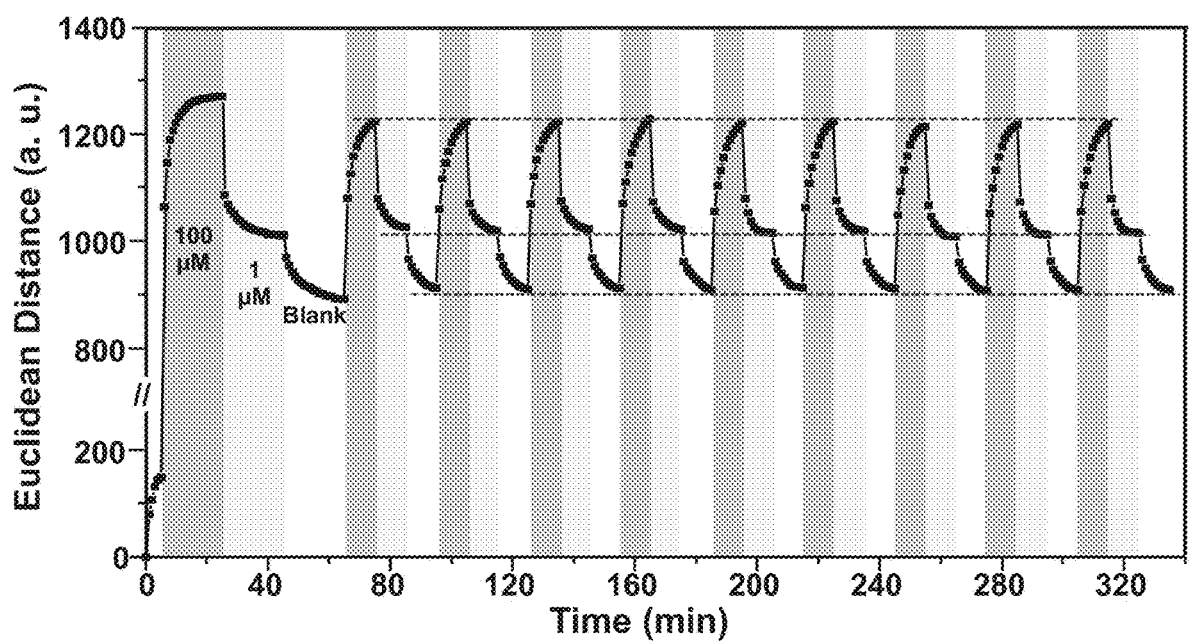
FIG. 11B illustrates the reversibility of sensor array response during 10 rounds of cycling for aqueous TMA exposure of a single array from the blank buffer to 100 µM, and then repeatedly from 100 µM to 1 µM and back to the blank. Data were acquired every 1 min; total response duration is 335 min; the total array response is represented by the total Euclidean distance of the 60-dimensional color difference vector. 90% of complete equilibration is achieved within 2 min of the first exposure to 10 ppm TMA and within 3 min for subsequent cycling between 10 and 1 ppm exposures. The blue lines are horizontal showing the lack of drift over 10 rounds of cycling.

The arrays were linearized for improved gas flow path and printed robotically (FIGS. 7A-B), then mounted on a snap-together, disposable cartridge (FIG. 1A); the low dead volume of this configuration greatly improves the array response time. Digital images of the arrays were acquired before and after exposure to diluted gas mixtures or aqueous solutions using an ordinary flatbed scanner (Epson Perfection V600, FIG. 1B and FIG. 8). Color difference maps were generated from changes in red, green and blue values of each spot upon exposure to analytes. FIGS. 2A-B shows sensor array responses (i.e., changes to the red, green, and blue values of the digital images) to a series of concentrations of gaseous and aqueous TMA after 2 min exposure: significant color changes were observed by naked eye even at sub-ppm level (FIG. 9). The biggest responses are from solvatochromic dyes (spot 1-2), pH indicators (spot 4-6 and 8-11) and metal-containing dyes (spot 16-18), which reflects the changes in local polarity, Brønsted basicity, and Lewis basicity, respectively, induced by the presence of TMA. Color difference maps as a function of TMA concentration are readily distinguished from one another even by eye before any statistical analysis. The response curves for both gaseous and aqueous TMA detection are more than 90% equilibrated within 2 min at most concentrations, based on total array response in Euclidean distance of the color difference patterns of the sensor array spot colors before compared to during or after exposure to the TMA source (FIGS. 10A-B). While the array is meant to be a disposable, it shows excellent reversibility between different concentrations of TMA (FIGS. 11A-B).

Figure 20:
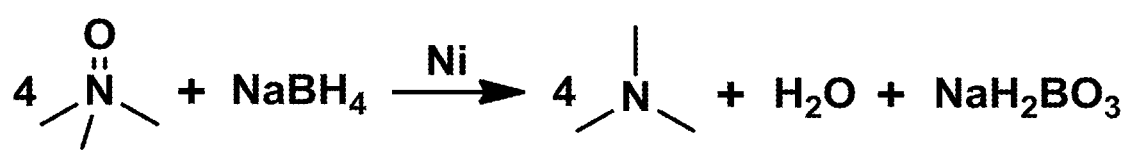
FIG. 20 depicts the chemical reduction of TMAO by sodium borohydride ($NaBH_4$) catalyzed by Raney Nickel, producing one molecule of TMA for every molecule of TMAO reduced.
Figure 21:
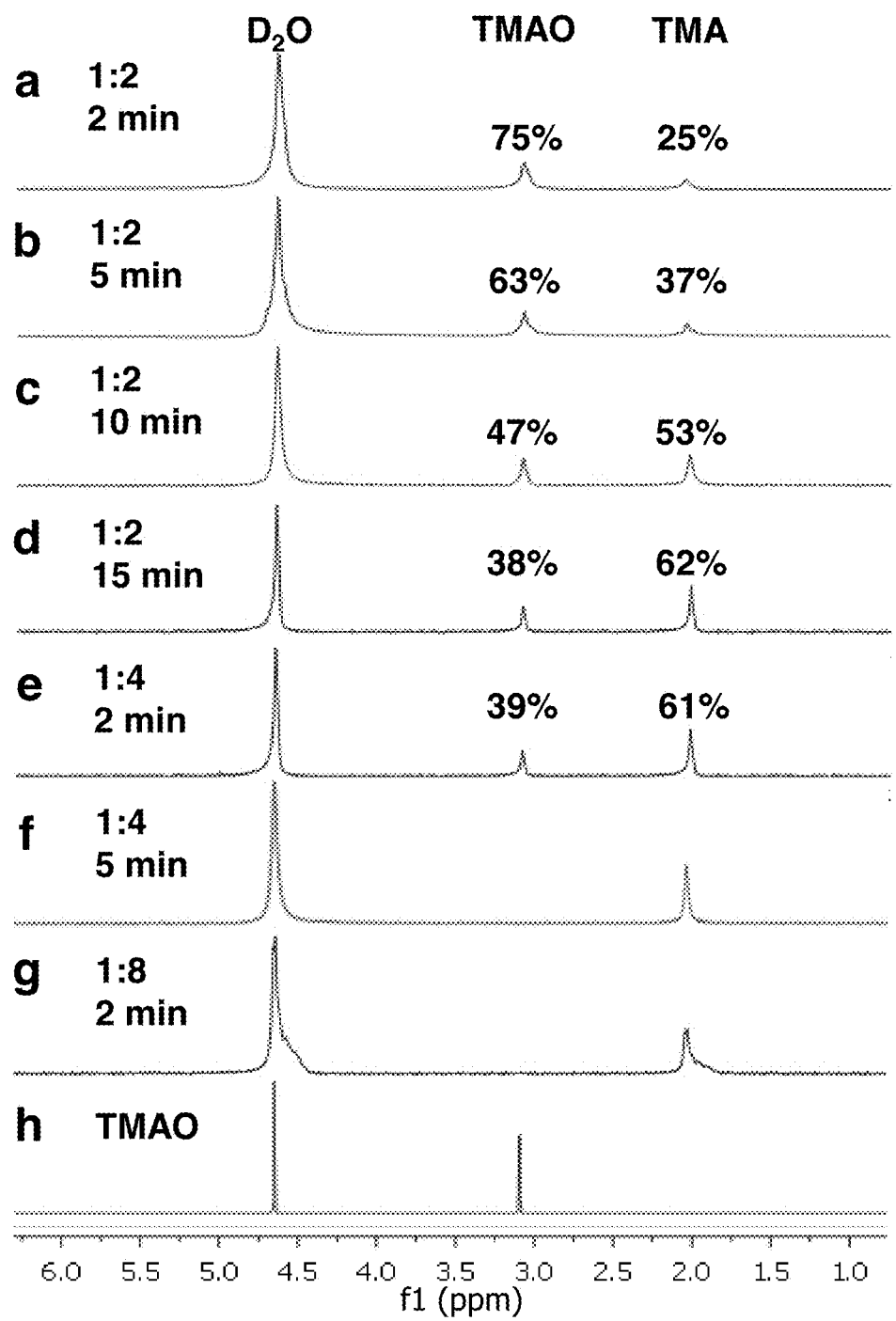
FIG. 21 shows the reduction of TMAO as demonstrated in the NMR spectra of the reduction reaction of a 1:2 molar ratio between TMAO and $NaBH_4$ at room temperature after 2 min (spectrum a); after 5 min (spectrum b); after 10 min (spectrum c); and after 15 min (spectrum d); of the reduction reaction of a 1:4 molar ratio between TMAO and $NaBH_4$ after 2 min (spectrum e); and after 5 min (spectrum and of the reduction reaction of a 1:8 molar ratio between TMAO and $NaBH_4$ after 2 min (spectrum g). Spectrum h depicts an exemplary NMR spectrum of standard TMAO control without reduction. The reduction reaction is complete within 2 min when the molar ratio between TMAO and $NaBH_4$ is 1:8. In all cases, starting concentration of TMAO was 200 µM and the amount of Raney Ni was 0.1 mg/mL.

An effective method for the rapid analysis of TMAO has been invented using a reductant ($NaBH_4$) and a catalyst (Raney Ni) to convert TMAO to TMA followed by analysis of volatile TMA as in the procedures already discussed. All TMAO can be converted to TMA within 2 min. with the addition of 8 molar equivalents of $NaBH_4$ (FIGS. 20 and 21). The reaction can readily proceed even at room temperature with a high yield (>95% in 2 minutes, FIGS. 22 and 23).

Figure 3:
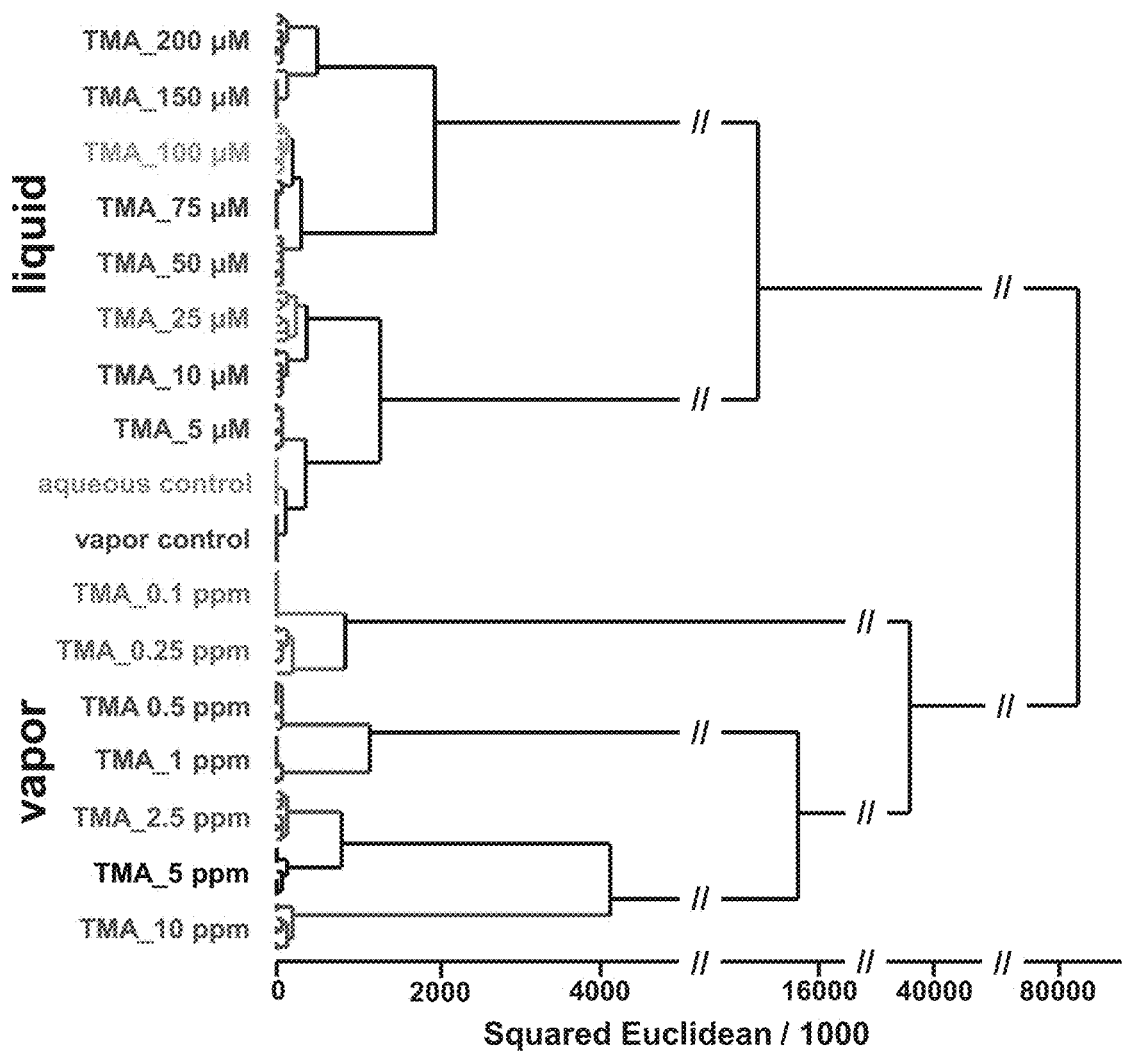
FIG. 3 illustrates an exemplary dendrogram of hierarchical cluster analysis for TMA at different concentrations in gases or in solutions with two controls based upon 119 trials, wherein all the concentrations were clearly discriminable against each other.

For a semi-quantitative analysis of the sensor array responses, we made use of a standard chemometric approach, hierarchical cluster analysis (HCA), to group color changes by concentration. The advantages of HCA are that it deals well with high dimensional data and is inherently model free in its analysis (i.e., unsupervised). The clustering of vectors is based on their positions in the 60-dimensional Euclidean space (i.e., the changes in RGB values for each of the 20 sensor array spots). FIG. 3 shows the HCA dendrogram for 2 min exposure to both gaseous and aqueous TMA. In septuplicate trials, all 15 TMA concentrations and two controls show tight clustering without error in clustering 119 cases. Even in the low concentration cases (5 and 10 µM of aqueous TMA; 0.1 and 0.25 ppm of gaseous TMA), good separation of clusters were still observed with no misidentifications.

A more sophisticated, but supervised, classification method, support vector machine (SVM) analysis, was used to create optimized classifiers. Unlike clustering methods such as HCA, SVM is a predictive method designed to classify new incoming data that is not part of the training database. SVM classification is based on pairwise class prediction and focuses on the data most likely to be misclassified (i.e., the so-called support vectors) using a specific transformation function (kernel) that best separates the data for any given pair of classes. Classification accuracy can be estimated using cross-validation methods that split the database and create classifiers based on training and evaluation data subsets. SVM results using a leave-one-out permutation method of cross-validation were performed. No misclassifications were found among either gaseous or aqueous samples: i.e., the error rate of predictive classification is <1% out of 119 trials.

Figure 12A:
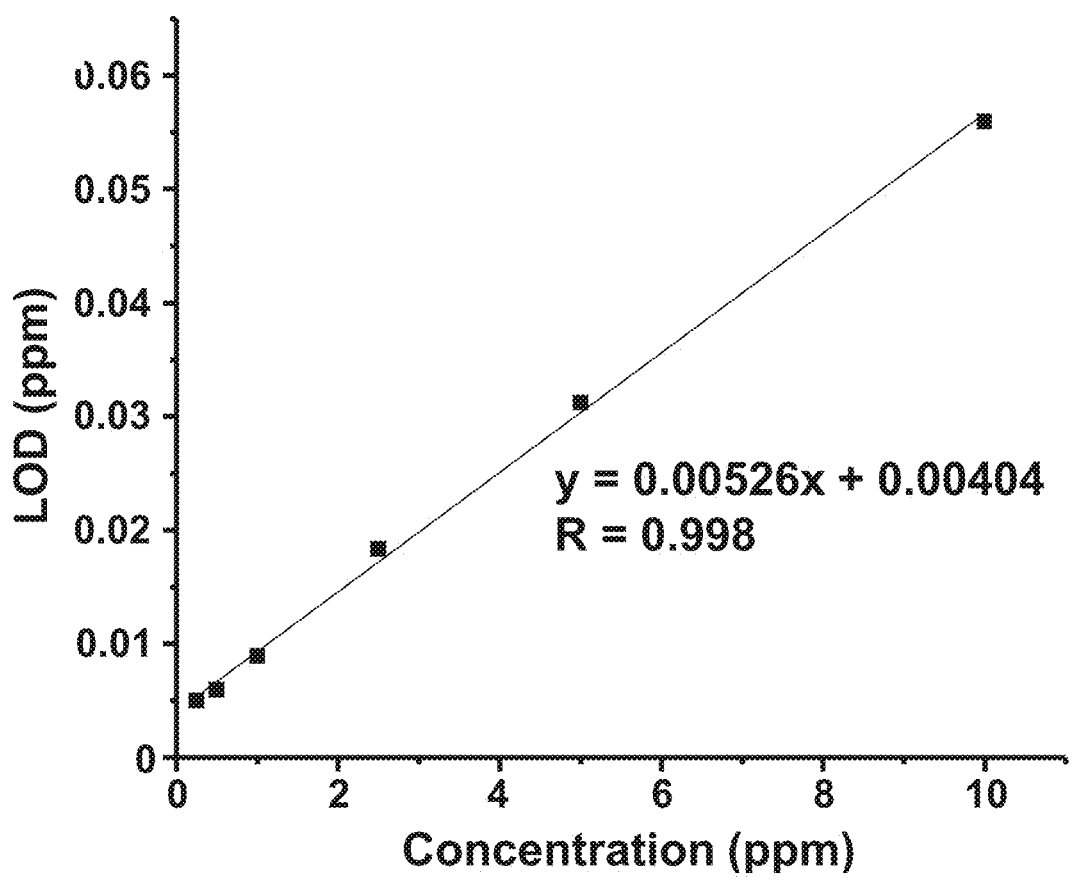
FIG. 12A depicts exemplary calibration curves for extrapolation of the LOD of gaseous TMA. Concentration ranges from 0.1 ppm to 10 ppm for gases and 5 µM to 200 µM for solutions. LOD of TMA is calculated to be 4 ppb in the gas and 2 µM in the solution.
Figure 12B:
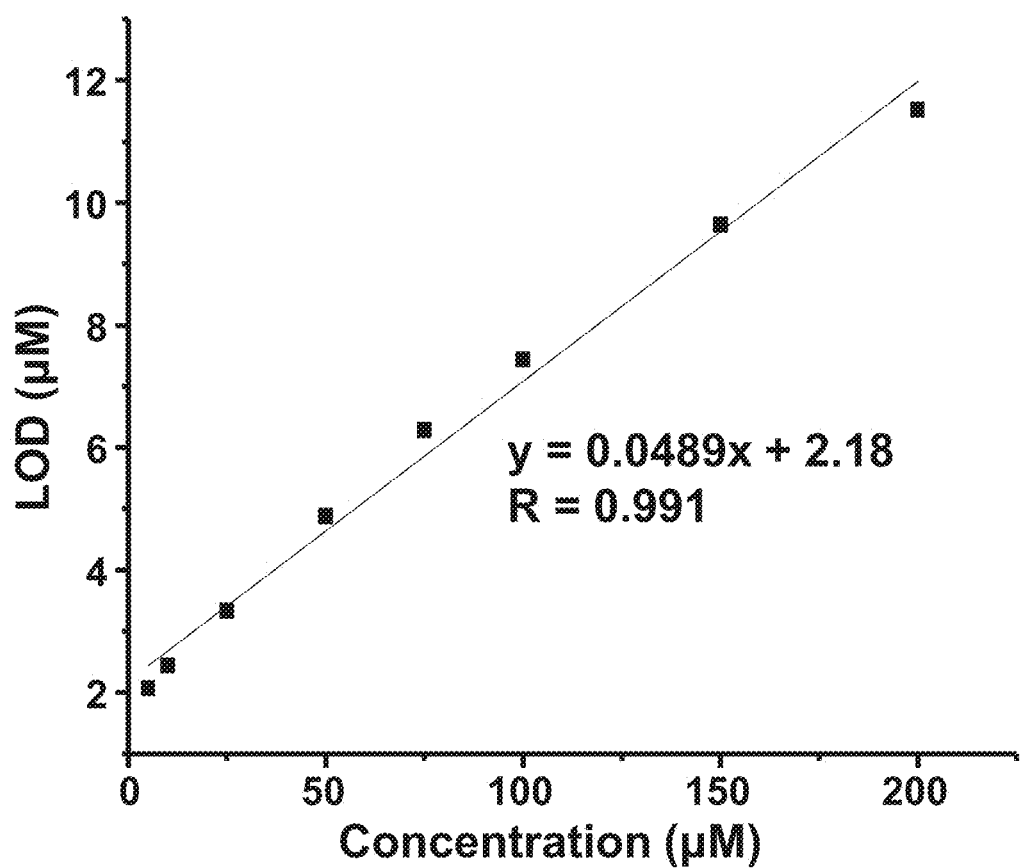
FIG. 12B depicts exemplary calibration curves for extrapolation of the LOD of aqueous TMA. Concentration ranges from 0.1 ppm to 10 ppm for gases and 5 µM to 200 µM for solutions. LOD of TMA is calculated to be 4 ppb in the gas and 2 µM in the solution.

We estimate the limits of detection (LODs) for gaseous and aqueous TMA by extrapolating from the observed array responses at relevant concentrations. We define the LOD as the concentration needed to give three times the S/N versus background for the largest response among the 60 color difference vectors. The calculated LODs for TMA are 4 ppb in gas phase and 2.3 µM in the aqueous media (FIGS. 12A-B). The LOD of TMA gas is comparable to the threshold of human olfactory receptors (2.5 ppb), while that of aqueous TMA is well below the threshold for the appearance of fish malodor symptoms (10 µg/mL, i.e., 169 µM). Our LODs are also well below the NIOSH/OSHA permissible exposure limit (PEL) of TMA, i.e., 10 ppm for long term exposure; as a toxic gaseous irritant, TMA can cause health issues such as headaches, nausea and skin burns.

To compare the two LODs obtained in different phases, Henry's law was employed to calculate the gaseous equivalent of the aqueous concentration. Using the appropriate Henry solubility constant (i.e., 0.47 mol m$^{-3}$ Pa$^{-1}$), the equilibrium partial pressure of TMA vapor above the aqueous solution at its LOD is estimated to be ~50 ppb, which is ~10-times higher than gaseous LOD. This reflects the effect of interference from water on the response of the sensor array.

Figure 13A:
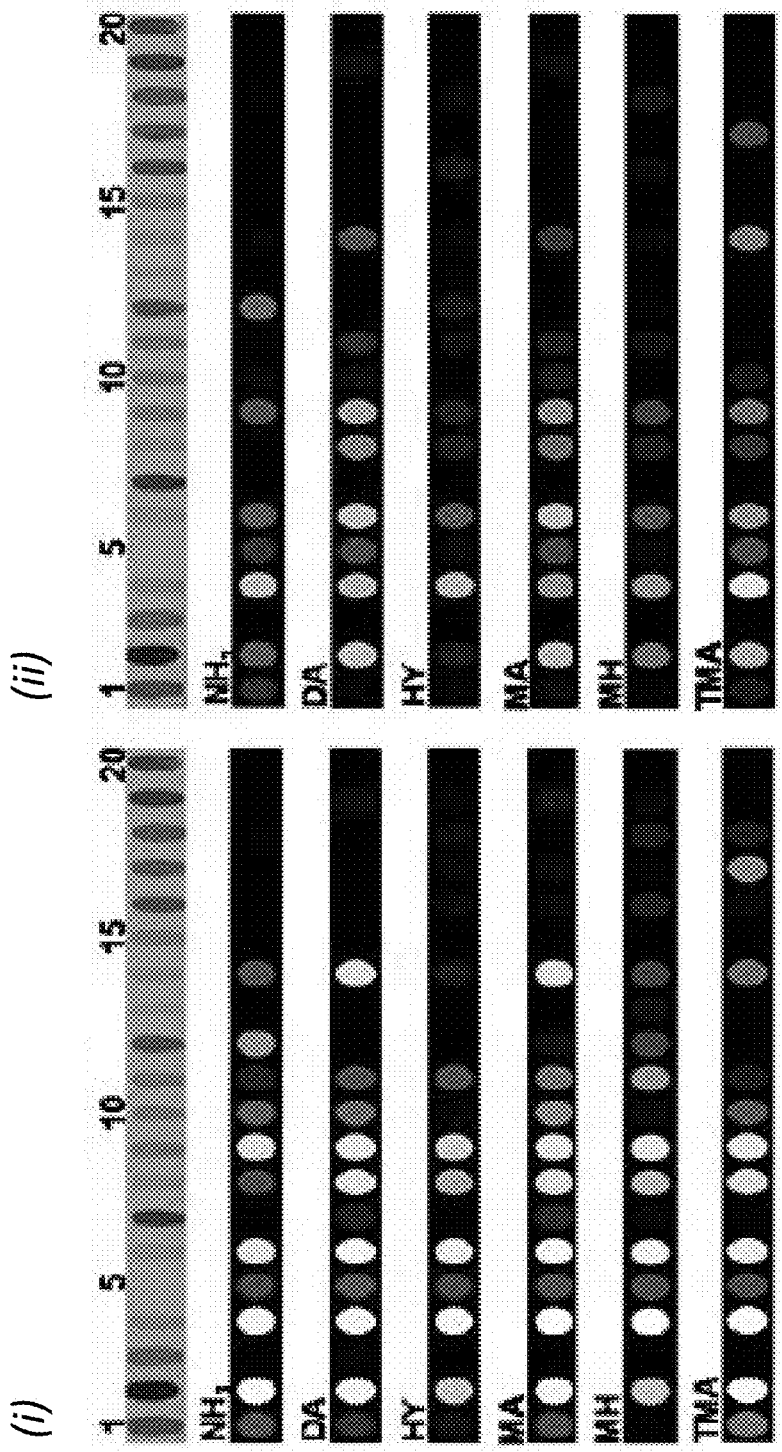
FIG. 13A depicts an average response of the sensor array to gaseous amines at 10 ppm (panel (i)) and 1 ppm (panel (ii)). Each sample was repeated in septuplicate trials. For visualization of the difference images, the color range is expanded from 4 to 8 bits per color (i.e., RGB color range of 4-19 expanded to 0-255).
Figure 13B:
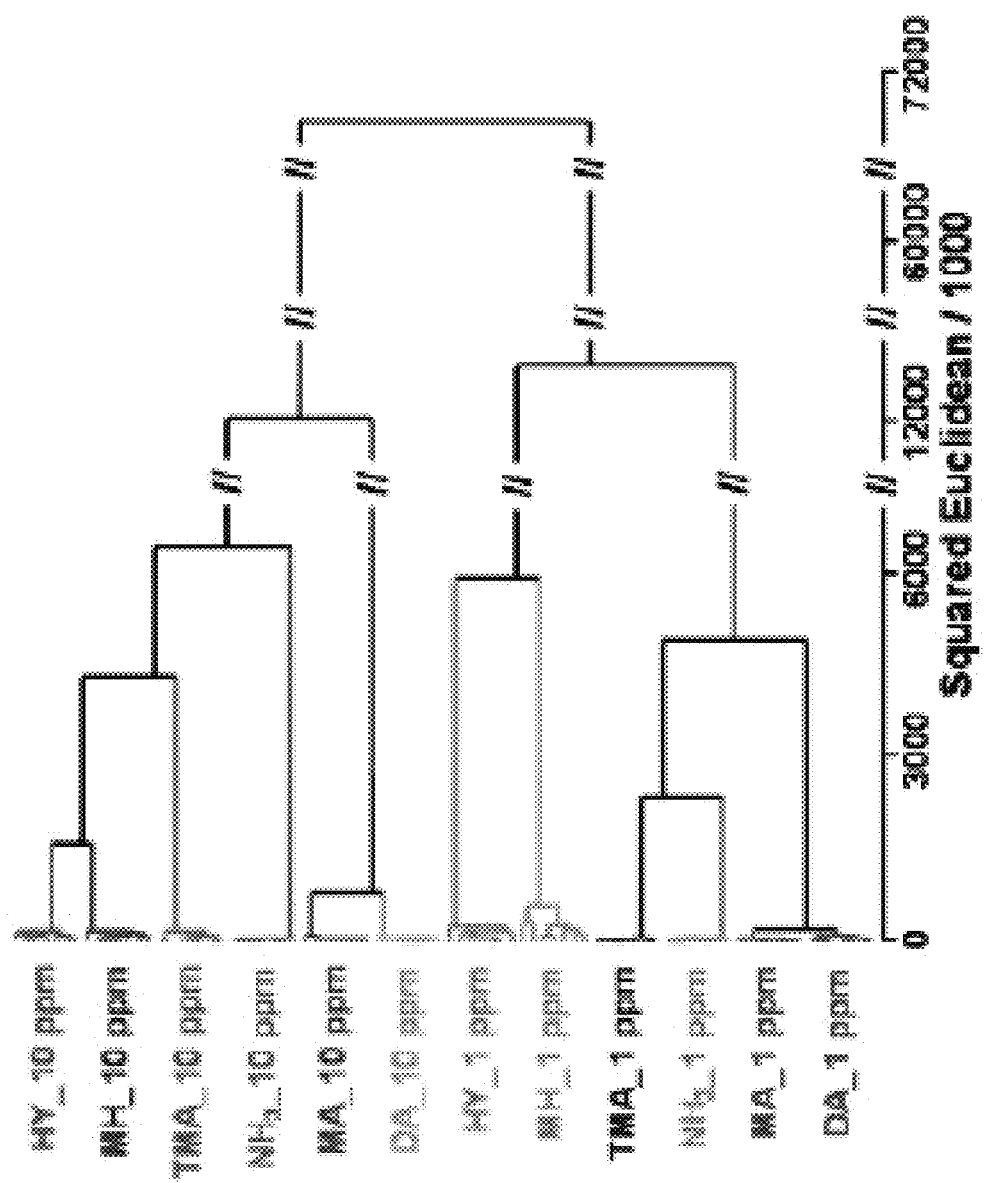
FIG. 13B depicts an exemplary dendrogram of hierarchical cluster analysis for gaseous amines at two concentrations. Each sample was repeated in septuplicate trials. For visualization of the difference images, the color range is expanded from 4 to 8 bits per color (i.e., RGB color range of 4-19 expanded to 0-255).
Figure 13C:
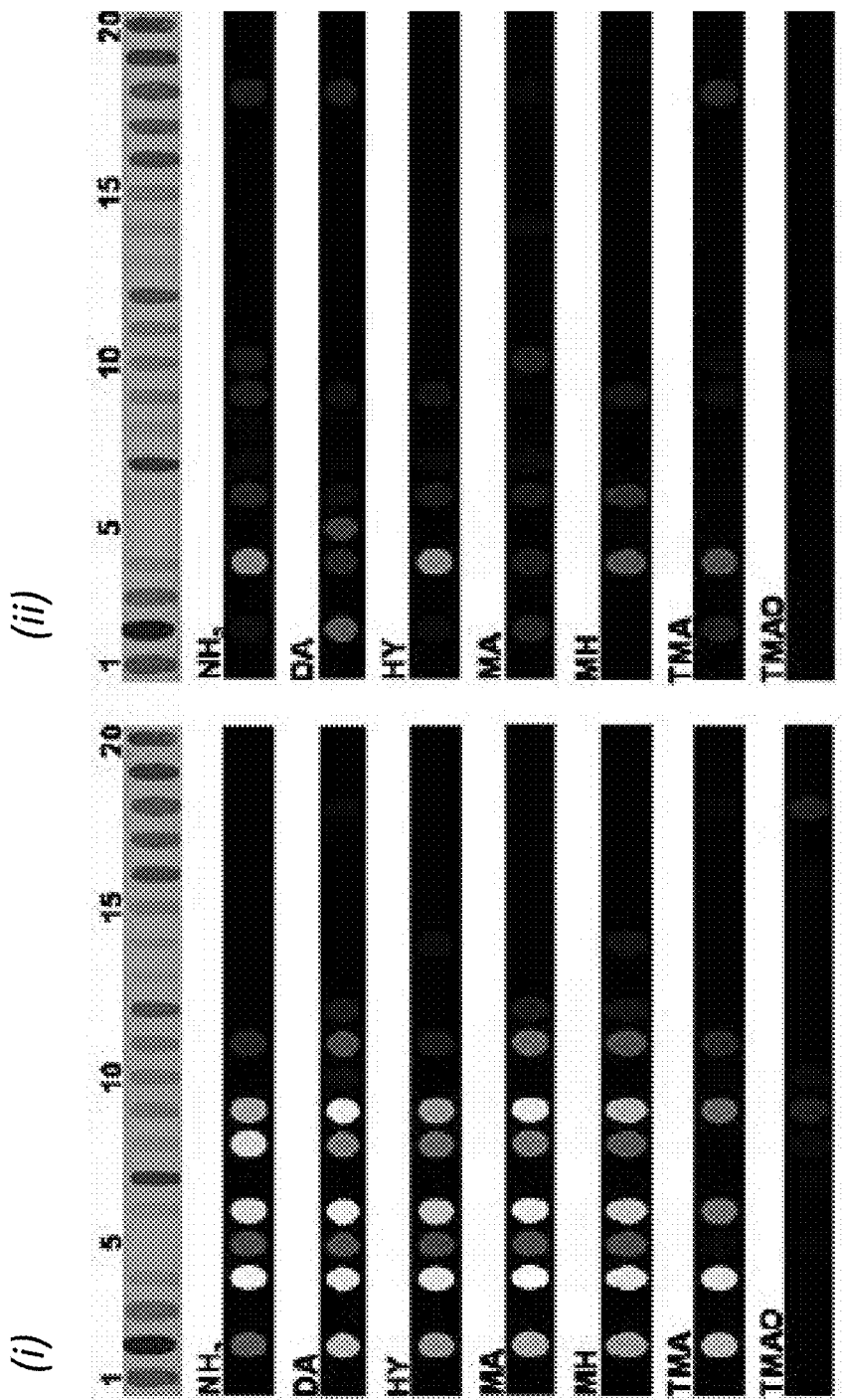
FIG. 13C depicts average responses of the sensor array to aqueous amines at 100 µM (panel (i)) and 10 µM (panel (ii)). Each sample was repeated in septuplicate trials. For visualization of the difference images, the color range is expanded from 4 to 8 bits per color (i.e., RGB color range of 4-19 expanded to 0-255).
Figure 13D:
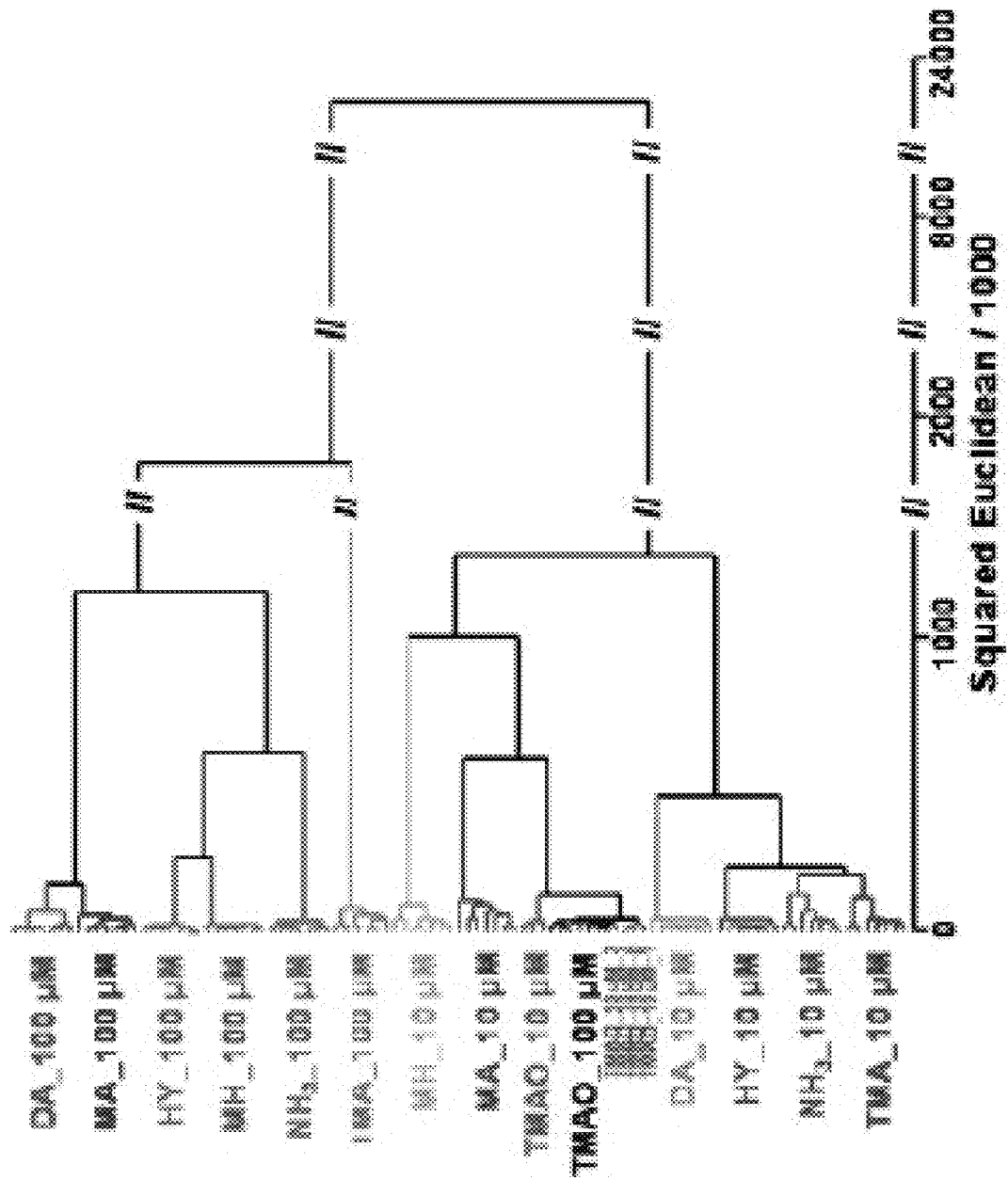
FIG. 13D depicts an exemplary dendrogram of hierarchical cluster analysis for aqueous amines at two concentrations. Each sample was repeated in septuplicate trials. For visualization of the difference images, the color range is expanded from 4 to 8 bits per color (i.e., RGB color range of 4-19 expanded to 0-255).

While LODs are well defined mathematically, they represent only the point at which the array detects something, but does not tell the identity of the analyte. The point at which one can discriminate one analyte from another is the limit of recognition (LOR), which is inherently less well-defined because it depends upon the library of analytes among which one wishes to differentiate. Here we have examined five representative amines (ammonia, dimethylamine (DA), methylamine (MA), hydrazine (HY) and methylhydrazine (MH)) as low molecular weight analogs to TMA, as well as its N-oxide metabolite, TMAO; all analytes were tested both in aqueous media and as gases (except the solid TMAO) at two concentrations (10 and 100 µM for solutions; 1 and 10 ppm for gases). The HCA dendrogram show that all gaseous amines are perfectly clustered (FIGS. 13A-D); among the aqueous samples, the array data do not differentiate between 10 µM and 100 µM trials of TMAO (FIG. 13D), presumably due to the relatively low sensitivity of our sensor array to TMAO, which is only a weak base ($pK_a$ 4.7). It is clear that the sensor array is able to distinguish TMA from other amines or TMAO in both gaseous and aqueous phases, and we conclude that the LOR for TMA vs. five similar amino odorants is well below 1 ppm in the gas phase and 10 µM in aqueous media.

Figure 4A:
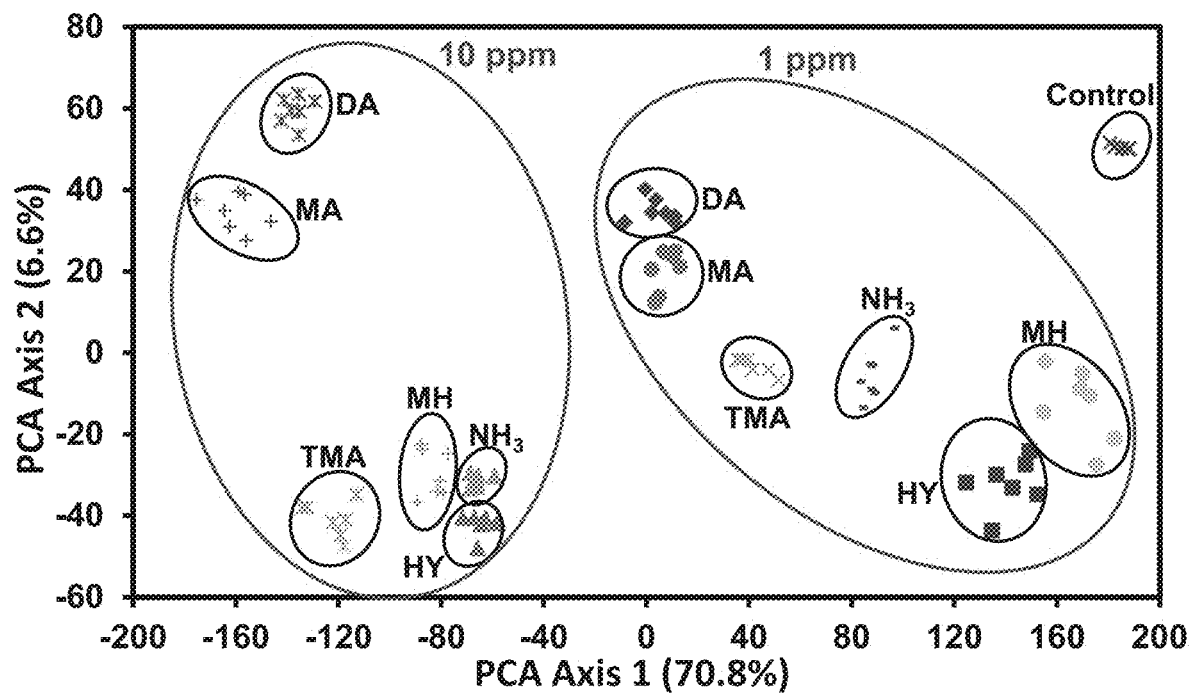
FIG. 4A illustrates two-dimensional principal components analysis score plot for septuplicate trials of gaseous amines at 10 ppm and 1 ppm and a control.
Figure 4B:
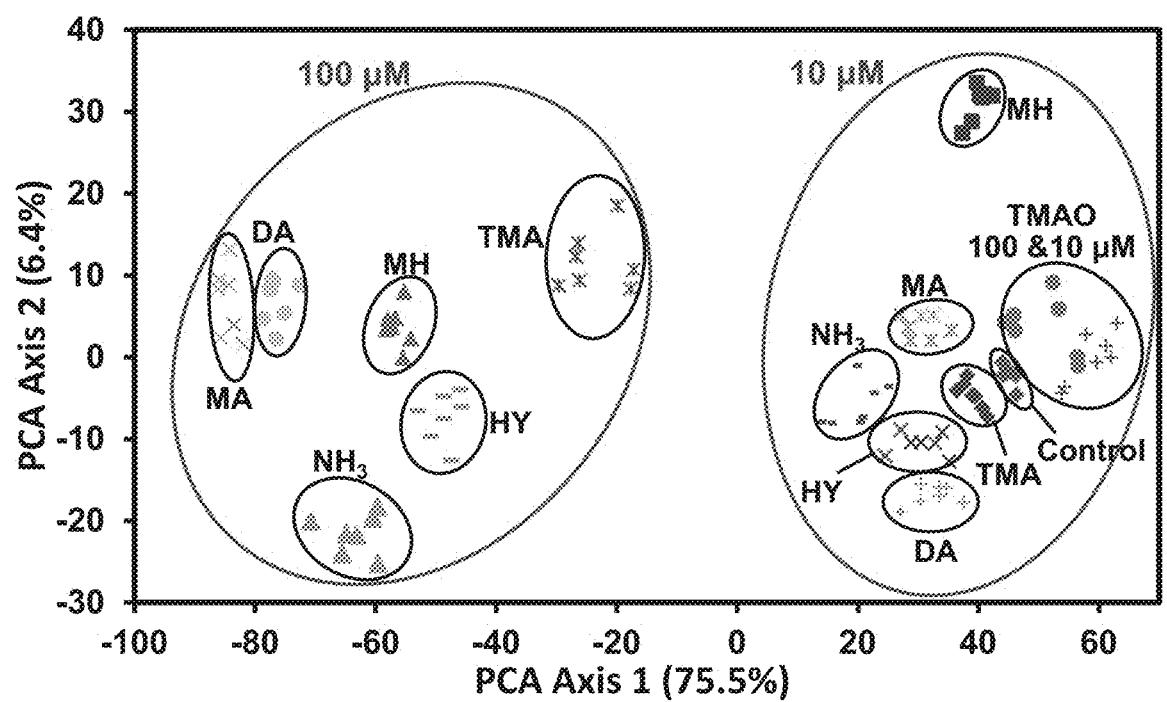
FIG. 4B illustrates two-dimensional principal components analysis score plot for septuplicate trials of aqueous amines at 100 μM and 10 μM and a control, wherein overlap is only observed between 10 μM and 100 μM TMAO.
Figure 14:
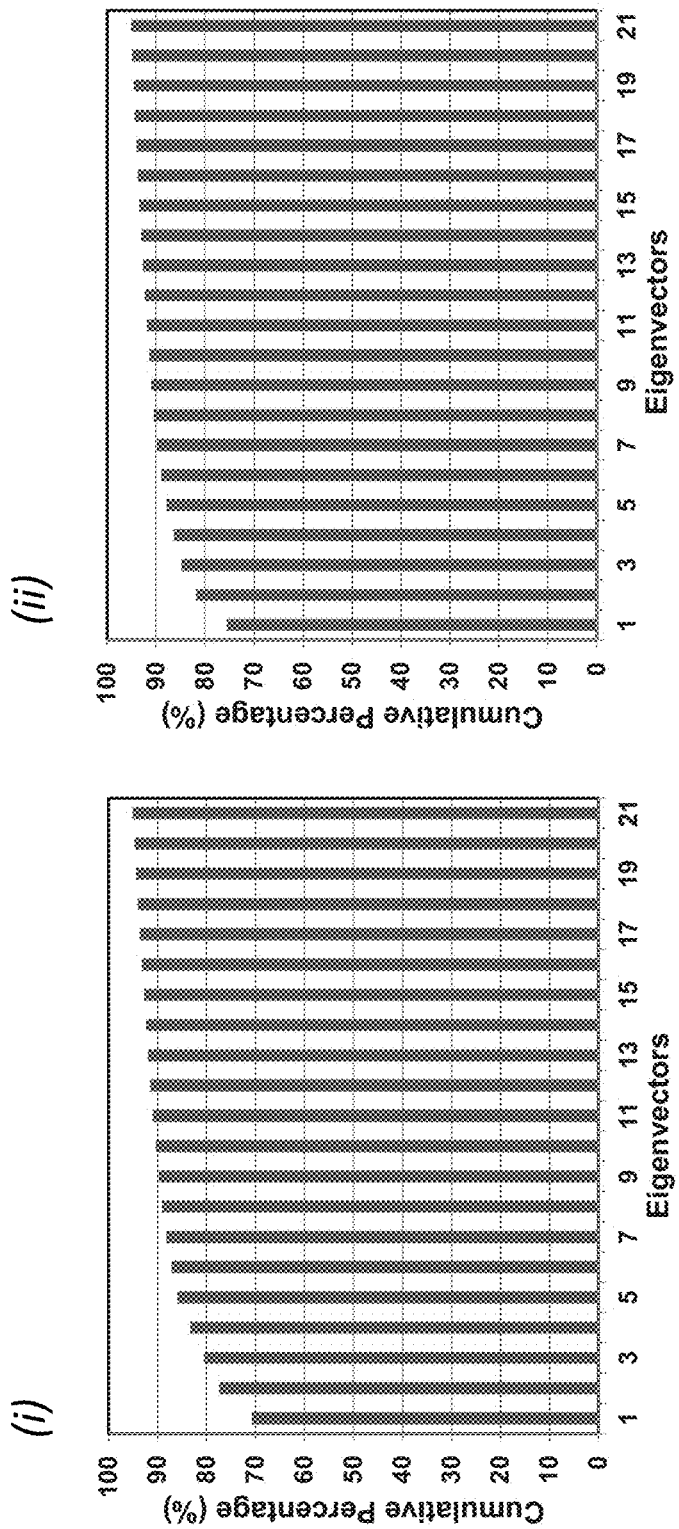
FIG. 14 depicts exemplary screen plots from a principal component analysis of all gaseous amines at 10 ppm and 1 ppm (panel (i)) and all aqueous amines at 100 µM and 10 µM (panel (ii)). Twenty-one dimensions are required to capture 95% of the total variance in both gaseous and aqueous cases, consistent with the wide range of analyte chemical properties probed by the sensor array.

To better elucidate the array's specificity towards TMA, principal component analysis (PCA) was performed to give a measurement of the dimensionality of the database. A relatively high dimensionality among various amines at two concentrations was expected and indeed observed (FIG. 14): 10 dimensions are required to capture 90% of the total variance of all gaseous samples and 8 dimensions for aqueous ones, which is consistent with the wide range of analyte chemical properties probed by the sensor array. In spite of the high dimensionality, good discrimination is provided even by just the first two principal components, as shown in FIGS. 4A-B. As with the HCA, all gaseous analytes were differentiable from each other, and all aqueous analytes were differentiable except for 10 and 100 µM TMAO.

Figure 15A:
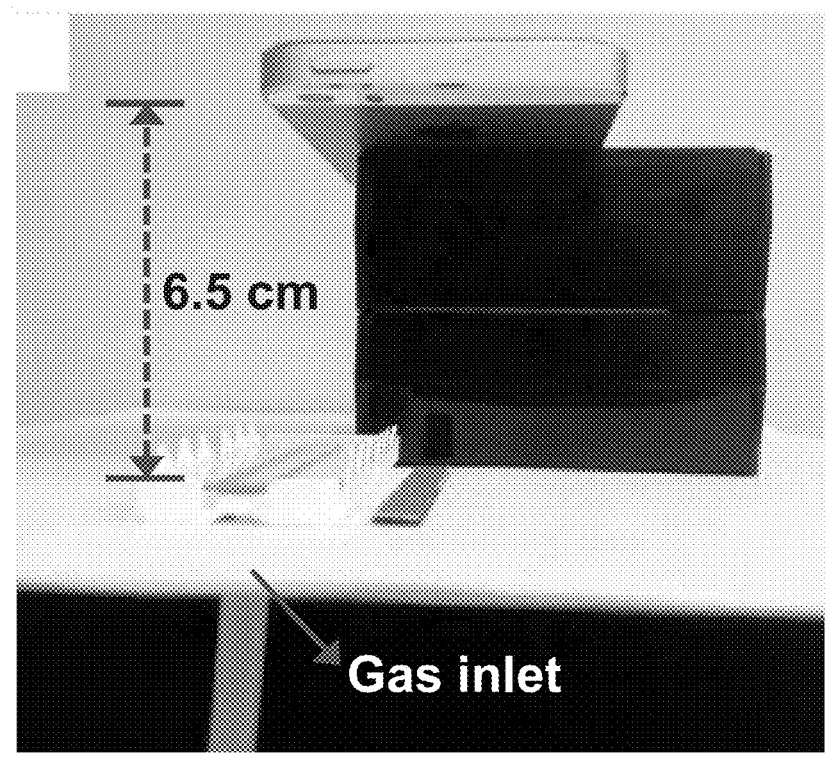
FIG. 15A illustrates an exemplary imaging set-up using an exemplary view of a cellphone scanning platform, wherein iPhone is 6.5 cm above the colorimetric sensor array.
Figure 15B:
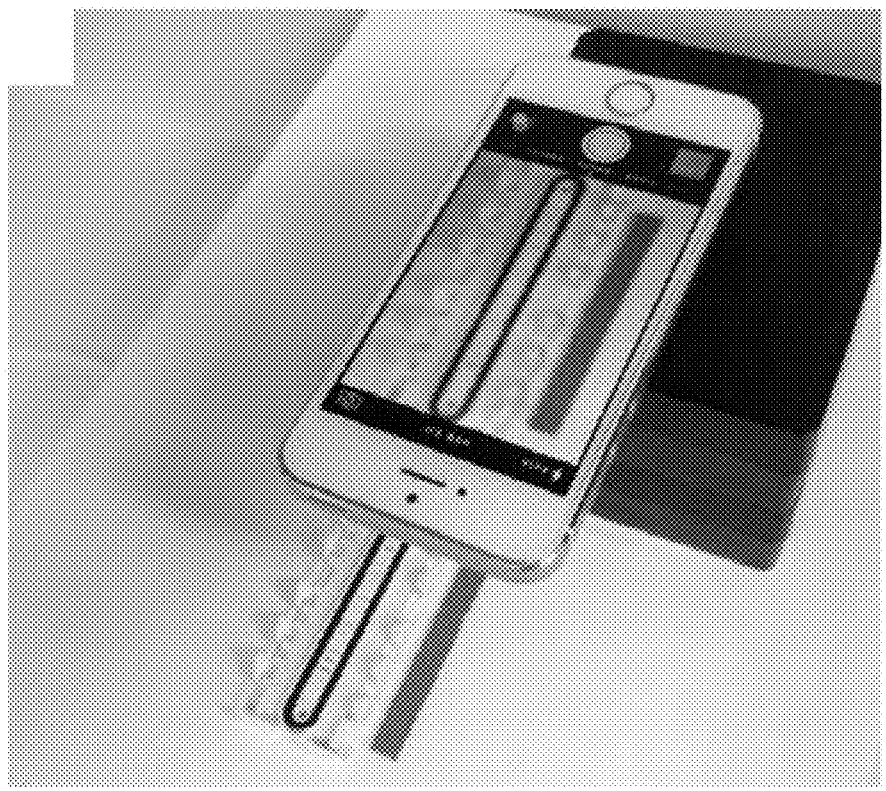
FIG. 15B illustrates an exemplary imaging set-up using an exemplary topview of a cellphone scanning platform, wherein iPhone is 6.5 cm above the colorimetric sensor array.
Figure 15C:
FIG. 15C illustrates an exemplary imaging set-up using an exemplary view of a handheld analyzer detection. The handheld device samples gas from polyethylene bags either containing 50% RH nitrogen (right) or TMA at a premixed concentration in 50% RH nitrogen (left).
Figure 16:
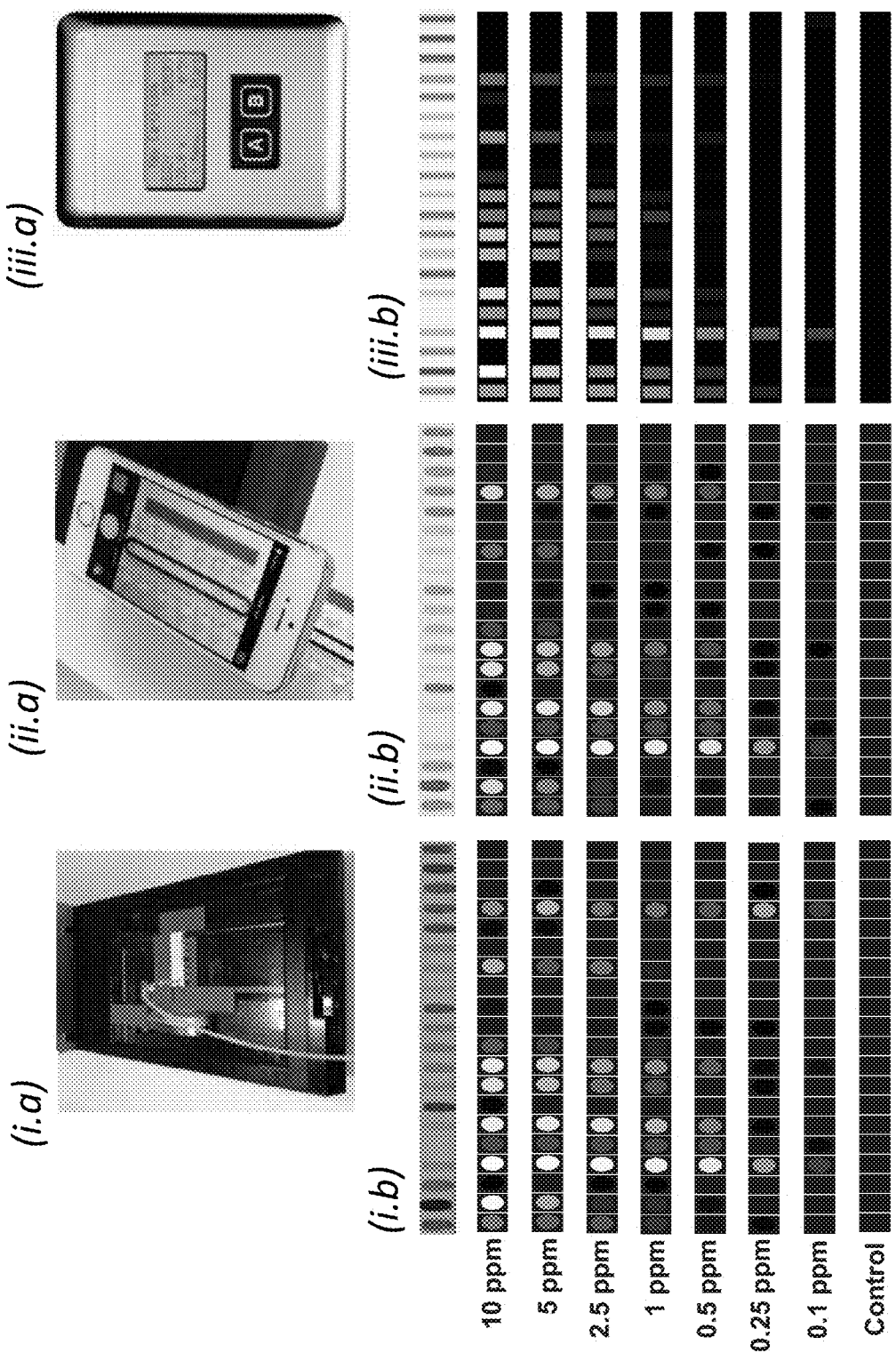
FIG. 16 depicts an average sensor array responses (panels (i.b), (ii.b) and (iii.b), respectively) of septuplicate trials after 2 min exposure to various concentrations of TMA collected by a flatbed scanner (panel (i.a), an iPhone 5s camera (panel (ii.a) and a handheld reader (panel (iii.a)), respectively. For visualization purposes, the color range is expanded from 4 to 8 bits per color (i.e., RGB color range of 4-19 expanded to 0-255).
Figure 17:
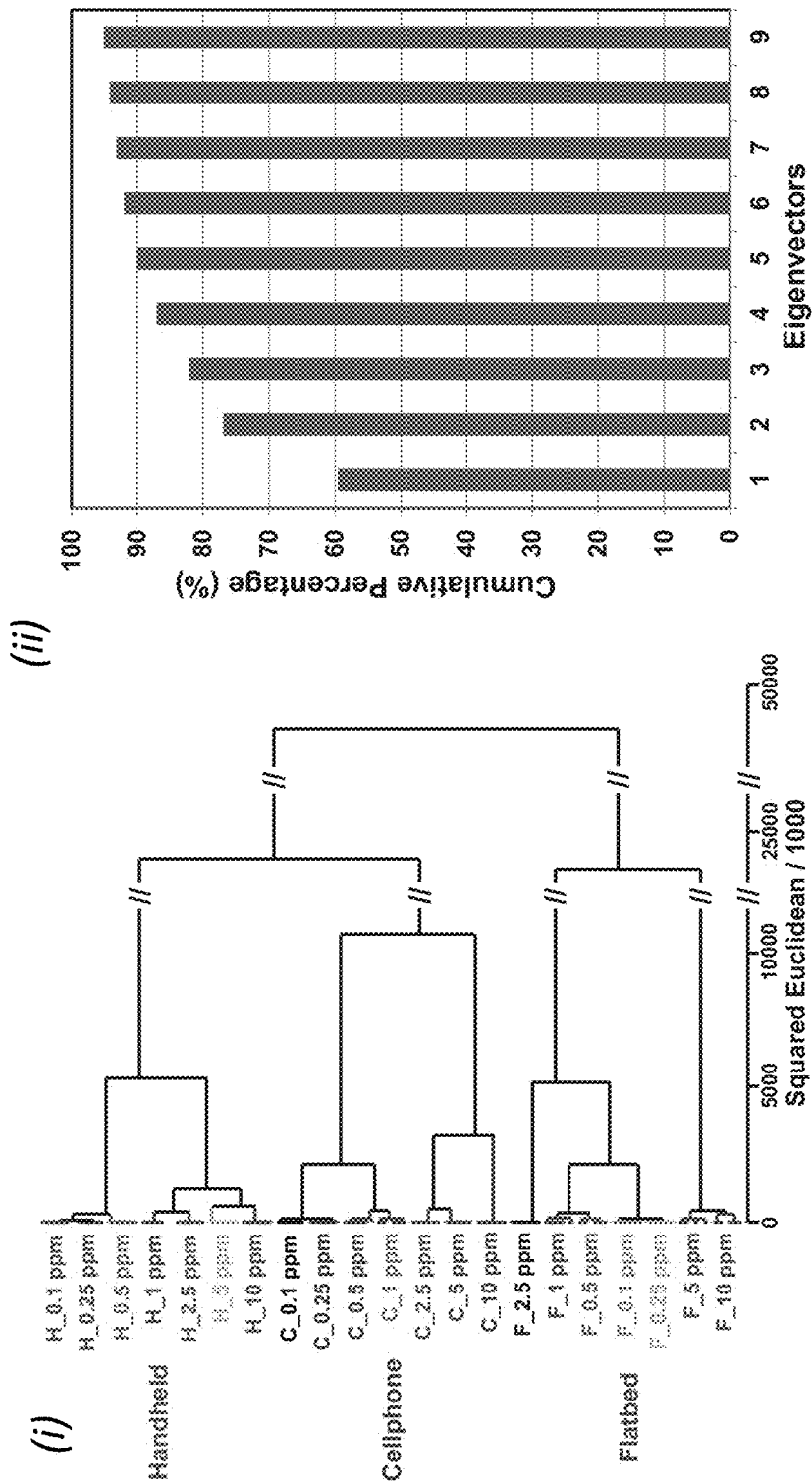
FIG. 17 depicts an exemplary dendrogram of hierarchical cluster analysis (panel (i)) and an exemplary dendrogram of screen plot of principal component analysis on the database of seven concentrations of TMA vapors collected by three scanning devices (panel (ii)).
Figure 18:
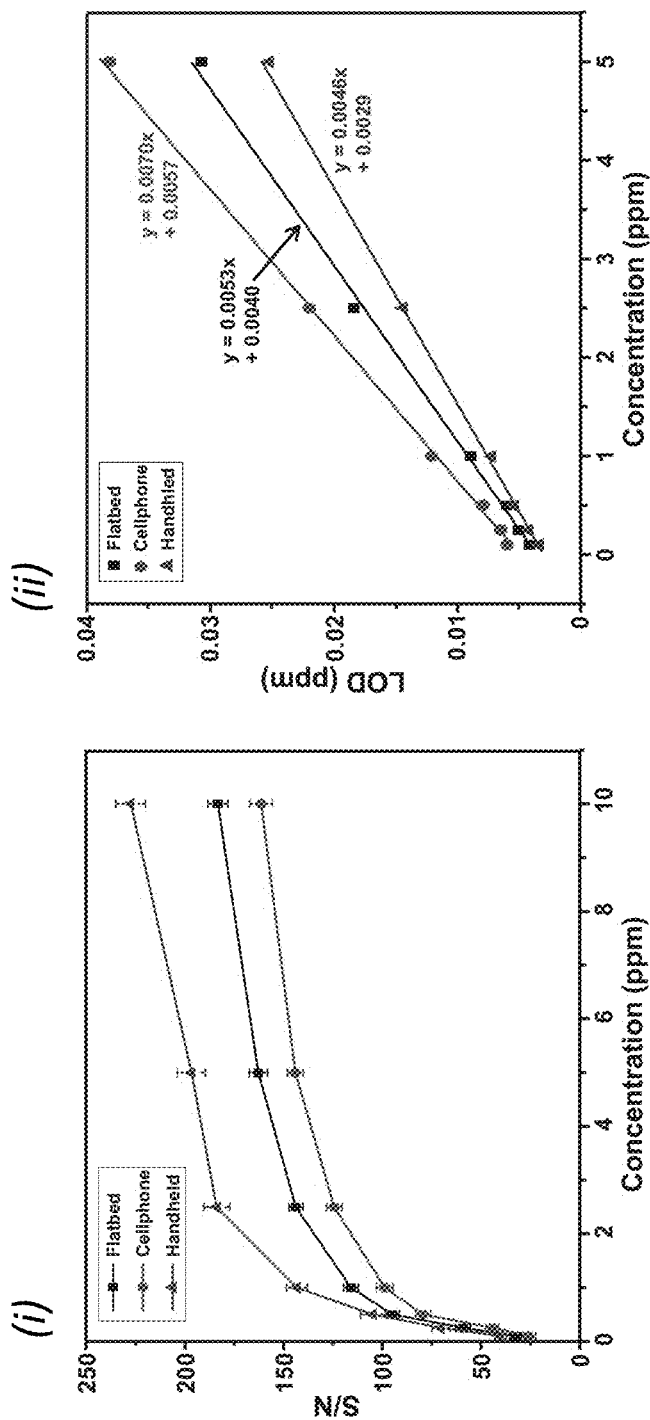
FIG. 18 illustrates an exemplary signal to noise ratios from the most responsive RGB channels observed in flatbed or iPhone detection as a function of TMA concentrations (panel (i)), wherein the average value with error bars set to 2 σ from quintuplicate trials is shown; exemplary calibration curves for extrapolation of the LOD of TMA vapors obtained by the three imaging devices (panel (ii)), wherein the LOD of TMA vapors is calculated to be 3 ppb for the handheld analyzer, 4 ppb for the flatbed scanner and 6 ppb for the iPhone.

For point of care diagnosis, portability of the imaging device is paramount. Towards that end, we have very recently developed a handheld reader (see Askim and Suslick, *Anal. Chem.* 2015, 87, 7810-7816 and WO 2015/034801, hereby incorporated by reference) which uses a diaphragm micropump to sample analyte gases and a color contact image sensor (CIS) to collect colorimetric data, FIGS. 15C, 16, and 17; the handheld reader has shown promising applications in the discrimination of home-made explosives. In addition, we have also examined the use of a cell phone camera (as shown in FIGS. 15A-B and 16), which has the added advantage of ready availability; cell phone imaging has just begun to find analytical applications. We therefore collected sensor array responses at designated concentrations of TMA vapors using our handheld reader and an iPhone 5s (FIGS. 15A-B), which both show similar sensor array response patterns to those collected by the flatbed scanner (FIG. 16); HCA gives 100% accuracy of clustering by scanning methods and then by TMA concentrations in 147 trials (FIG. 17). LOD measurements show the sensitivity of three devices to TMA vapors: handheld scanner, 3 ppb; flatbed, 4 ppb; cellphone, 6 ppb (FIGS. 17 and 18).

Figure 19:
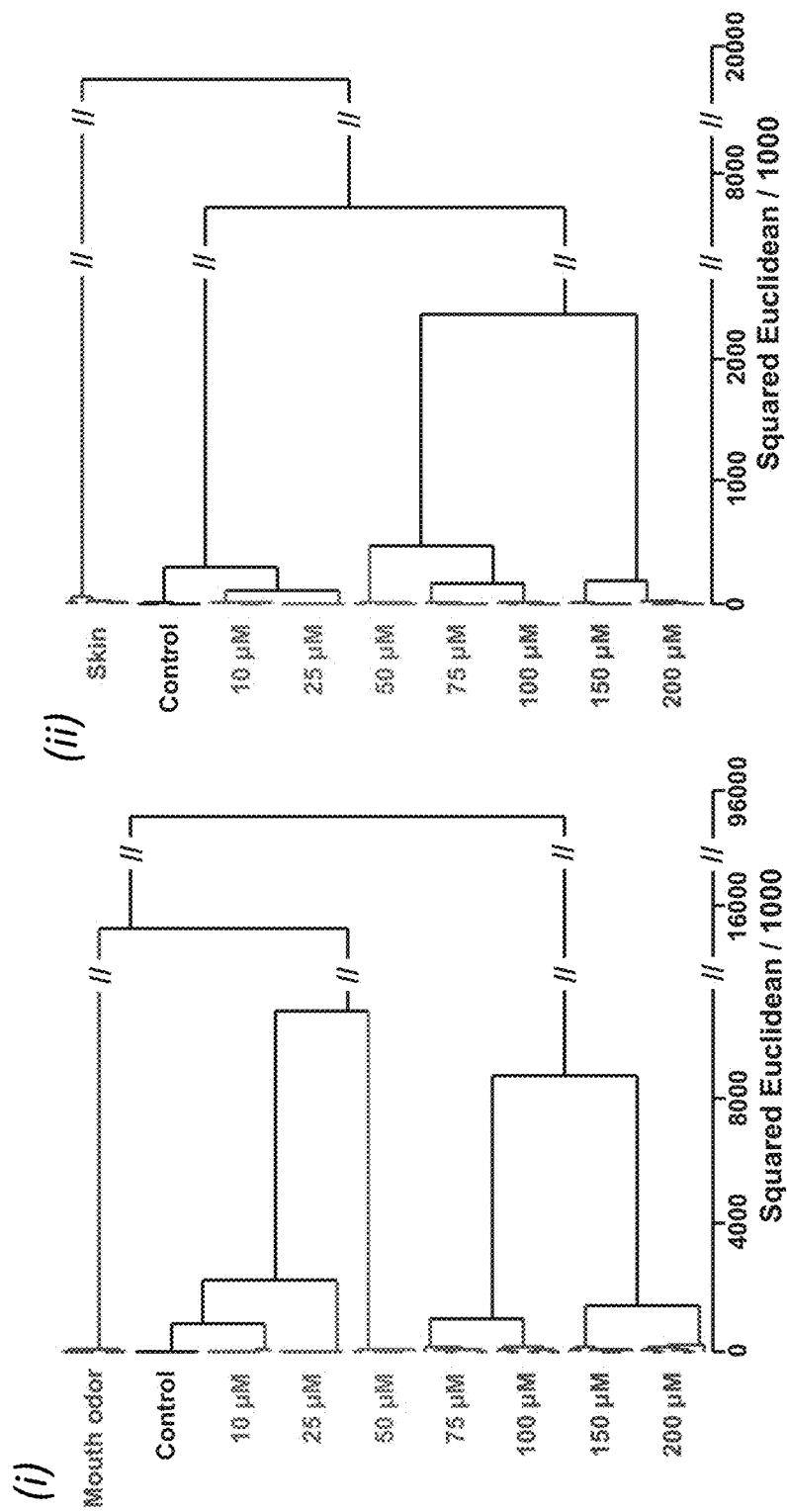
FIG. 19 depicts exemplary dendrograms of hierarchical cluster analysis for a dataset of simulated mouth odor test (panel (i)) and a dataset of simulated skin odor test (panel (ii)).

In a simulation of skin or mouth odor test for diagnosis of trimethylaminuria, we used this handheld reader to monitor the volatiles from filter papers soaked in TMA solutions or headspace TMA vapors (FIGS. 5A-B). Mouth odor simulations generally gain higher responses than skin ones after two min exposure. In patients with trimethylaminuria, the threshold for fish malodor symptoms is defined at TMA concentrations in urine of 10 µg/mL, i.e., 169 µM. Our simulations (FIGS. 5A-B and 19) show clear discrimination among diagnostically significant concentrations of TMA, blank and healthy controls, with calculated detection limits of ~5 µM for mouth odor simulations and ~2 µM for skin ones, which are comparable to the results obtained from the flatbed scanner.

Example 2

Materials and Methods for TMA Analysis

Array preparation. All reagents were analytical-reagent grade, purchased from Sigma-Aldrich and used as received. Preparation and robotic printing of colorimetric sensor arrays (FIGS. 7A-B) have been described in detail elsewhere (Askim et. al. *Chem. Sci.* 2016, 7, 199-206). The chemoresponsive dyes used in each spot is elaborated in Table 1 along with a color-coded legend indicating the expected chemical reactivity of each spot; visualized image captured by handheld device is shown in FIGS. 5A-B.

Analytes generation. All gases at their selected concentrations were prepared by mixing the gas stream of prediluted analyte with dry and wet nitrogen gas using MKS digital mass-flow controllers to achieve the desired concentrations and relative humidity at a total flow rate of 500 sccm (FIG. 8). Gas flow was running for 30 min to achieve a stabilized concentration before each measurement. Analytes concentrations were confirmed by in-line analysis with FTIR using a MKS multigas analyzer (model 2030). Solutions of TMA and other amines were prepared in 1×PBS (10 mM, pH 7.4) by spiking the corresponding amount of solutes into the stock buffer solution to achieve the desired vapor or liquid concentrations.

Data obtained on flatbed scanner. The arrays were imaged as a function of time on an ordinary flatbed scanner (Epson Perfection V600); the before-exposure image was acquired after 2 min exposure of wet $N_2$ at 50% relative humidity or blank buffer; after-exposure images were acquired with full equilibration after exposure to the targeted vapor or aqueous concentrations. Difference maps were obtained by subtracting the red, green, and blue (RGB) values of before-exposure images from those of after-exposure images; the diameter of each sensor array spot was ~50 pixels, the values of which were averaged. Color differences was digitized using a customized software package, SpotFinder 1.0.6 (iSense LLC., Mountain View, Calif.). Septuplicate trials were taken for each analyte or concentration.

Data obtained on iPhone 5s. Sensor array images were collected using the camera of an Apple iPhone 5s. The same exposure procedures and data process protocols used for the flatbed scanner were applied to the cell phone detection, except that RGB values of each sensor array element (e.g., spot) were corrected using the equation $R_{corr}=R_i/R_{white}*255$, in which $R_i$ is the initial RGB value of the sensor array element (e.g., spot) while $R_{white}$ is the RGB value of the white reference; white reference for each sensor array element (e.g., spot) is taken from the white blank area on each side of the sensor array element (e.g., spot). The correction method is used to minimize inconsistencies of brightness from image to image due to changes in ambient lighting, as well as the inconsistency of lighting among sensor array elements (e.g., spots) within each single image caused by non-uniform illumination across the array.

Data obtained on handheld reader. The experimental setup using the handheld imaging device is shown in FIG. 8. The construction and specifications of the handheld device used in this study have been elaborated in recent publications (Askim and Suslick, *Anal. Chem.* 2015, 87, 7810-7816). Raw data was normalized using a calibration created from a one-time measurement of a 0% reflectance standard (i.e., the sensor array with all LEDs turned off) and a 100% reflectance standard (i.e., a white blank array). For visualization, difference maps were constructed by taking the absolute value of the reflectance measurements before and during 2 min exposure and scaling a relevant color range to the 8-bit color scale (i.e., 0-255); for all statistical analyses, the actual values of the reflectance measurements were used without modification. For SN measurements, signal and noise were calculated for each data channel using all trials in the data set (i.e., red, green, and blue values of 20 sensor array elements (e.g., spots); 60 dimensions in total); signals for each channel were defined as the difference between each analyte trial measurement and the average of the non-exposed controls, and noise was defined as the standard deviation among the control data; septuplicate trials were taken for each analyte or concentration.

Database analysis. The chemometric analysis was performed on the color difference vectors using the Multi-Variate Statistical Package™ (MVSP v.3.1, Kovach Computing); in all cases, minimum variance (i.e., "Ward's Method") was used for HCA clustering. Support vector machine (SVM) analysis was carried out using a leave-one-out permutation method based on an open-source SVM library, LIBSVM (Chang and Lin, *ACM Trans. Intell. Syst. Technol.* 2011, 2, 1-27).

Example 3

Procedures and Methods for TMAO Analysis

Figure 22:
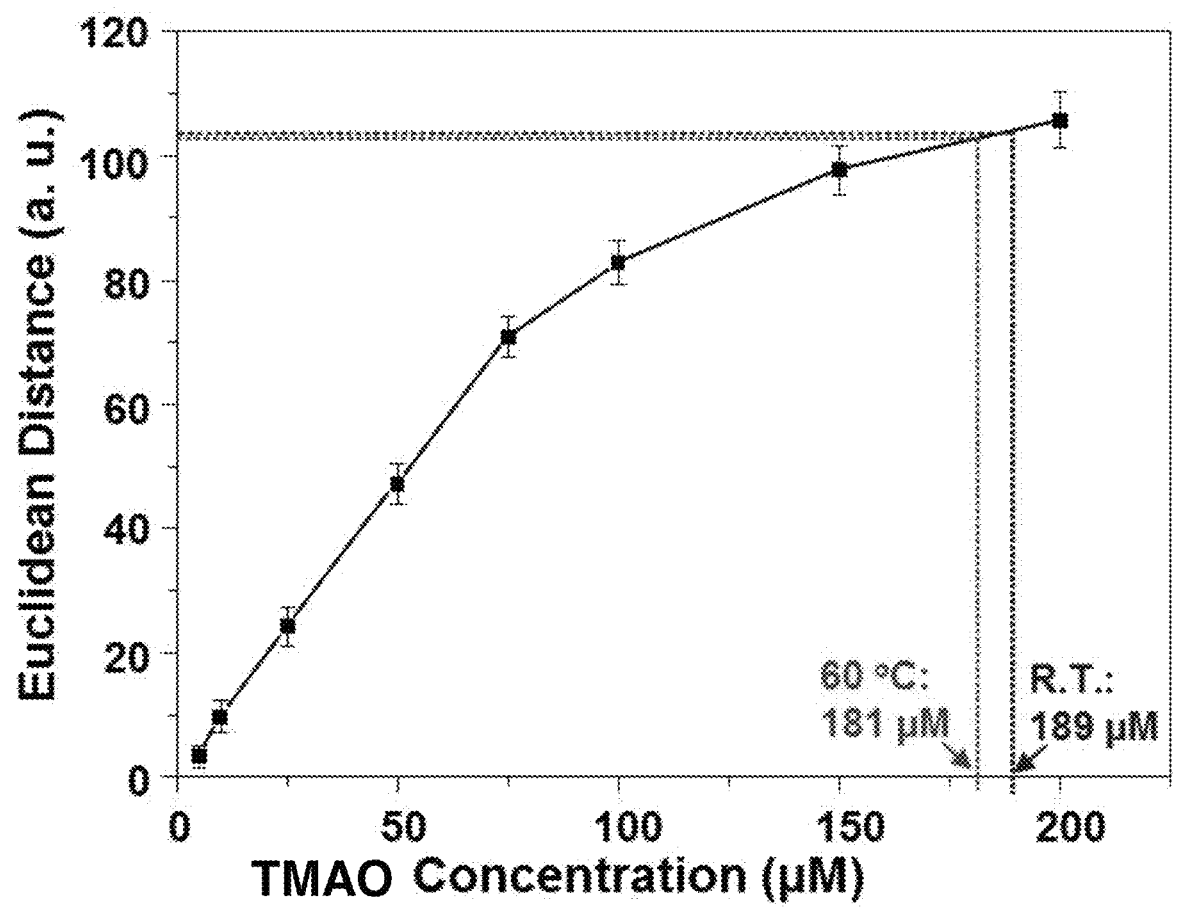
FIG. 22 shows the final concentration of TMA after reduction at room temperature or 60° C. The determination of TMA concentration is made by comparison of the observed sensor array response (i.e., the total Euclidean distance of the changes in red, green and blue values of all of the sensor array spots) to known TMAO concentrations. The reduction of TMAO to TMA occurs rapidly even at room temperature with a yield of 95% at room temperature.

A device as substantially shown and described herein offers a possible approach for accurate and rapid quantification of TMAO in a typical biological sample with the presence of multiple amino components, i.e., a simulated urine sample. Simulated urine consists of various inorganic salts (e.g., sodium chloride, disodium phosphate, monopotassium phosphate, etc.), volatile amines (e.g., ammonia, TMA, dimethylamine, etc.), involatile amines (e.g., TMAO) and organic compounds (e.g., creatinine, uric acid and urine, etc.). The method exemplified here aims to evaporate all volatile amines, redissolve involatile species (which includes TMAO), and reduce TMAO to TMA using a highly specific reductant and catalyst (e.g., sodium borohydride and Raney nickel, FIG. 20) that selectively targets N-oxides. Based on our study, extremely high conversion rates and yields can be achieved within 2 min with the addition of 8 molar equivalences of reductant (FIG. 21); the yield is >95% at room temperature (FIG. 22).

As shown in FIG. 23, 0.1 mL simulated urine sample was dropped on a rectangular filter paper strip (5×1 cm), which saturates the filter paper. After drying in air in a 20 mL scintillation vial at ambient condition for 10 min to remove all volatile components, 0.3 mL nanopure water was added to rinse the filter paper and redissolve involatile residues. The filter paper was then removed and a clear, reconstituted solution was formed in the vial with the volume of ~0.2 mL. TMAO was converted to TMA by treating with Raney nickel (0.01 mg) and sodium borohydride (0.05 mg) and analyzed using the linearized colorimetric sensor array as delineated in Examples 1 and 2 above. The molar ratio between TMAO and the reductant was set to ~1:20 to guarantee effective reduction.

INCORPORATION BY REFERENCE

All of the patents, patent applications, patent application publications, other publications and citations of data publicly available in government-, academic- or industry-supported data bases recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. A method for detection and quantification of trimethylamine (TMA) and other volatile amines or derivatives of TMA, the method comprising:
   passing a sample over a sensor array, said sensor array comprising:
   a substrate; and
   a plurality of chemically responsive dyes or colorants,
   wherein the plurality of chemically responsive dyes or colorants are selected from the group consisting of Tetraiodophenolsulfonephthalein, Rosolic Acid, Pyrocatechol Violet, and 4-[2-[4-(dimethylamino)phenyl]ethenyl]-2,6-dimethylpyrylium to produce changes in color in the sensor array; and
   detecting changes in color using an image sensor to determine the amount of TMA and other volatile amines or derivatives of TMA in the sample.

2. The method of claim 1, wherein the sample is selected from a group consisting of sweat, saliva, urine, vapor from breath, air blown in from the surrounding area, water vapor, air from a room or area to be tested, air in proximity to a test subject, and air in proximity to a test object.

3. The method of claim 1, wherein the plurality of chemically responsive dyes or colorants is arranged in a linear array.

4. The method of claim 1, wherein the image sensor is selected from a hand-held device, a cell phone, a flatbed scanner and a computer-connected imaging device.

5. The method of claim 1, wherein the substrate comprises a highly porous sol-gel formulation.

6. A method for diagnosing trimethylaminuria (TMAU) in a subject, the method comprising:
   passing a sample from a subject over a sensor array, said sensor array comprising:
   a substrate; and
   a plurality of chemically responsive dyes or colorants,
   wherein the plurality of chemically responsive dyes or colorants are selected from the group consisting of Tetraiodophenolsulfonephthalein, Rosolic Acid, Pyrocatechol Violet, and 4-[2-[4-(dimethylamino)phenyl]ethenyl]-2,6-dimethylpyrylium to produce changes in color in the sensor array;
   detecting changes in color using an image sensor to determine the amount of TMA or derivatives of TMA in the sample;
   wherein the presence of TMA or derivatives of TMA detected in the sample above a predetermined concentration range is indicative of a positive diagnosis of a patient having TMAU.

7. A sensor array for detection of trimethylamine (TMA), the sensor array comprising:
   a substrate; and
   a plurality of chemically responsive dyes or colorants,
   wherein the plurality of chemically responsive dyes or colorants are selected from the group consisting of Tetraiodophenolsulfonephthalein, Rosolic Acid, Pyrocatechol Violet, and 4-[2-[4-(dimethylamino)phenyl]ethenyl]-2,6-dimethylpyrylium.

8. The sensor array of claim 7, wherein the sensor array is a disposable cartridge.

9. A device for detection of trimethylamine (TMA), the device comprising:
   a sensor array of claim 7,
   an image sensor in optical communication with the sensor array for determining a spectral response of the optically-responsive chemical sensing elements, the image sensor comprising at least one light emission source, and
   electronics in electrical communication with the image sensor,
   wherein the electronics is configured with a non-transitory tangible computer readable medium having computer readable program code for analyzing spectral response data.

10. A device for detection of TMA, the device comprising:
    the sensor array of claim 7, said sensor array arranged as a linear array;
    an image sensor in optical communication with the linear array for determining a spectral response of the optically-responsive chemical sensing elements, the image sensor comprising at least one light emission source; and electronics in electrical communication with the image sensor, wherein the electronics is configured with a non-transitory tangible computer readable medium having computer readable program code for analyzing spectral response data.

11. The device of claim 10, wherein the linear array is configured in a disposable cartridge.

12. A device for quantifying trimethylamine (TMA) and trimethylamine oxide (TMAO), said device comprises:

a colorimetric sensor array, said sensor array comprising:
a substrate; and
a plurality of chemically responsive dyes or colorants,
wherein the chemically responsive dyes or colorants are selected from the group consisting of Tetraiodophenol-sulfonephthalein, Rosolic Acid, Pyrocatechol Violet, and 4-[2-[4-(dimethylamino)phenyl]ethenyl]-2,6-dimethylpyrylium;

an imaging device; and an electronic device configured with a non-transitory tangible computer readable medium having computer readable program code for analyzing spectral response data, wherein the imaging device is configured in optical communication with the colorimetric sensor array and in electrical communication with the electronic device.

13. The device of claim 12, wherein the imaging device is selected from a group consisting of a flatbed scanner, a digital camera, a CMOS (complementary metal-oxide-semiconductor) imaging sensor, a CCD (charge coupled device) imaging sensor, and a CIS (contact image sensor).

14. The device of claim 12, wherein the electronic device is selected from a group consisting of a computer, a cell phone and a handheld reader.

15. A method for the quantification of involatile TMAO by the initial removal of volatile amines, including TMAO, the method comprising:

air or other gas sparging or evaporation of a liquid sample to produce a residue;

re-dissolution of the residue in an aqueous solution to form a reconstituted sample;

reducing TMAO to TMA in the reconstituted sample; and analyzing the volatile TMA so produced with the device of claim 12.

16. The method of claim 15, wherein the step of reducing TMAO comprising use of a reductant being selected from a group consisting of sodium borohydride, or other related derivatives including salts of cyanoborohydride or triethylborohydride or tri-isopropylborohydride, lithium aluminum hydride, sodium bis(2-methoxyethoxy)aluminum hydride (Red-Al) and diiso-butylaluminum hydride (Dibal-H).

17. The method of claim 16, wherein the use of a reductant occurs in the presence of a transition metal catalyst, Raney Nickel, platinum, palladium as nanoparticles or colloids or supported on supports such as alumina, silica, or activated carbon.

* * * * *